(12) United States Patent
Endo

(10) Patent No.: US 11,379,977 B2
(45) Date of Patent: Jul. 5, 2022

(54) MEDICAL IMAGE PROCESSING DEVICE

(71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 76 days.

(21) Appl. No.: 16/852,517

(22) Filed: Apr. 19, 2020

(65) Prior Publication Data

US 2020/0242766 A1 Jul. 30, 2020

Related U.S. Application Data

(63) Continuation of application No. PCT/JP2018/038061, filed on Oct. 12, 2018.

(30) Foreign Application Priority Data

Oct. 20, 2017 (JP) .............................. JP2017-203863

(51) Int. Cl.
*G06K 9/00* (2022.01)
*G06T 7/00* (2017.01)
(Continued)

(52) U.S. Cl.
CPC ........ *G06T 7/0012* (2013.01); *A61B 1/00006* (2013.01); *A61B 1/04* (2013.01);
(Continued)

(58) Field of Classification Search
CPC ............... G06T 7/0012; G06T 2200/24; G06T 2207/30096; A61B 1/00006; A61B 1/04;
(Continued)

(56) References Cited

U.S. PATENT DOCUMENTS 9,503,692 B2    11/2016 Morita et al.
2005/0207645 A1  9/2005 Nishimura et al.
(Continued)

FOREIGN PATENT DOCUMENTS

JP    2004188026    7/2004
JP    2006129950    5/2006
(Continued)

OTHER PUBLICATIONS

"International Search Report (Form PCT/ISA/210) of PCT/JP2018/038061," dated Nov. 13, 2018, with English translation thereof, pp. 1-5.
(Continued)

*Primary Examiner* — Sean M Conner
*Assistant Examiner* — Han Hoang
(74) *Attorney, Agent, or Firm* — JCIPRNET

(57) ABSTRACT

A notification control unit includes a notification setting information selection unit, a notification setting information storage unit, a notification setting information setting unit, and the notification execution unit. Notification setting information is associated with individual setting information to be preserved in the notification setting information storage unit. The notification execution unit performs a notification according to setting of use-notification setting information which is selected by using the individual setting information by the notification setting information selection unit. The created or changed notification setting information is preserved in the notification setting information storage unit.

14 Claims, 22 Drawing Sheets

(51) Int. Cl.
  *A61B 1/00* (2006.01)
  *A61B 1/04* (2006.01)
  *A61B 1/06* (2006.01)
(52) U.S. Cl.
  CPC ............ *A61B 1/06* (2013.01); *G06T 2200/24* (2013.01); *G06T 2207/30096* (2013.01)
(58) Field of Classification Search
  CPC ..... A61B 1/06; A61B 1/00188; A61B 1/0638; A61B 1/043; A61B 1/0646; A61B 1/00009; A61B 1/00039; A61B 1/00055
  See application file for complete search history.

(56) References Cited

U.S. PATENT DOCUMENTS

| | | |
|---|---|---|
| 2006/0280347 A1 | 12/2006 | Shirahata et al. |
| 2016/0042122 A1* | 2/2016 | Sato ........................ G16H 30/40 715/781 |
| 2018/0098690 A1 | 4/2018 | Iwaki |

FOREIGN PATENT DOCUMENTS

| | | |
|---|---|---|
| JP | 2009072369 | 4/2009 |
| JP | 2011104016 | 6/2011 |
| JP | 2012000291 | 1/2012 |
| JP | 3194808 | 12/2014 |
| JP | 2016045573 | 4/2016 |
| JP | 2016062488 | 4/2016 |
| JP | 2016172077 | 9/2016 |
| WO | 2005011501 | 2/2005 |
| WO | 2016199273 | 12/2016 |

OTHER PUBLICATIONS

"Written Opinion of the International Searching Authority (Form PCT/ISA/237) of PCT/JP2018/038061," dated Nov. 13, 2018, with English translation thereof, pp. 1-9.

"Office Action of Japan Counterpart Application", dated Oct. 27, 2020, with English translation thereof, pp. 1-8.

"Office Action of Japan Counterpart Application", dated Aug. 3, 2021, with English translation thereof, pp. 1-6.

* cited by examiner

SOUND: LOUD
DISPLAY TIME: 10 SECONDS (NOTIFICATION: NONE)

MEDICAL IMAGE PROCESSING DEVICE

CROSS-REFERENCE TO RELATED APPLICATIONS

This application is a Continuation of PCT International Application No. PCT/JP2018/038061 filed on 12 Oct. 2018, which claims priority under 35 U.S.C. § 119(a) to Japanese Patent Application No. 2017-203863 filed on 20 Oct. 2017. The above application is hereby expressly incorporated by reference, in its entirety, into the present application.

BACKGROUND OF THE INVENTION

1. Field of the Invention

The present invention relates to a medical image processing device in which setting and changing of a notification method at the time of notifying a user of a medical image are easy.

2. Description of the Related Art

In the current medical field, a medical image processing device using a medical image, such as an endoscope system comprising a light source device, an endoscope, and a processor device is widespread. In recent years, by performing image analysis on the medical image, a region of interest as a target for diagnosis is detected and a notification to a user is performed. Further, the presence or absence and the type of a lesion, an observation state of a subject, and the like may be notified.

In the notification to the user as described above, it is necessary to perform a notification such that the user does not overlook a lesion or the like appearing in the medical image. In contrast, for example, in JP2006-129950A, an image display device is disclosed which prevents overlooking of a specific image by notifying a user using a notice sound including a preliminary announcement sound, a notification sound, and an end sound or vibration in a case where an image to be noticed such as a lesion image is displayed on display means in a system which a large number of images as images of a capsule endoscope are displayed in order. In addition, WO2005/011501A (corresponding to US2006/280347A1) discloses a medical image diagnosis device which selectively diagnoses a deformed part of an organ part appearing in a medical image and notifies of a change in shape of the diagnosed part using a screen display, a sound, or the like, thereby improving diagnosis efficiency while preventing overlooking of the medical image. Further, JP2016-172077A discloses an endoscope system which automatically changes setting of image processing in a specific endoscope depending on the RFID tag that an operator carries in a case where the image processing is performed on an image by the endoscope, thereby preventing overlooking by individual operators.

SUMMARY OF THE INVENTION

However, as in JP2006-129950A and WO2015/011501A, in a case where a user is notified by a notice sound when an image is displayed according to a predetermined criterion, it is necessary to individually set selection items for a notification image for appropriate image diagnosis each time due to, for example, the difference in techniques used by the user to perform diagnosis using the images, or the difference in cases to be diagnosed, and thus there is a problem of complexity. Therefore, as a method of setting various settings individually, a method which can automatically change setting of image processing of each operator at the time of acquiring an image by an endoscope is disclosed (JP2016-172077A). In this manner, the image may be easy to see and the lesion or the like may be difficult to overlook, but there is no description for a notification. Accordingly, in a case where a notification to the user is performed for appropriate medical image diagnosis, it is required to perform appropriate settings including not only how to perform a notification itself, but also what to notify.

An object of the invention is to provide a medical image processing device which can prevent overlooking of a lesion or the like by easily performing setting and changing of a notification method for notifying a user in a case where a region of interest as a target for diagnosis is detected from a medical image.

A medical image processing device according to an aspect of the invention includes an image acquisition unit, an image analysis processing unit, a notification execution unit, a notification setting information storage unit, and a notification setting information selection unit. The image acquisition unit acquires a medical image including a subject. The image analysis processing unit performs image analysis processing on the medical image. The notification execution unit notifies a user of a result of the image analysis processing according to notification setting information. The notification setting information storage unit preserves the notification setting information in association with individual setting information different from the notification setting information. The notification setting information selection unit selects use-notification setting information by using the individual setting information, from the notification setting information preserved in the notification setting information storage unit. The notification execution unit performs a notification according to setting of the use-notification setting information.

It is preferable that the individual setting information is user information relating to the user. It is preferable that the individual setting information is patient information of a patient having the subject. In addition, it is preferable that the individual setting information is part information representing a part. Further, it is preferable that the individual setting information is procedure information representing a procedure performed at a time of acquisition of the medical image.

It is preferable that the image analysis processing unit includes a region-of-interest detection unit that detects a region of interest from the medical image as the image analysis processing, and a lesion determination unit that determines lesion information indicating content of a lesion for the region of interest as the image analysis processing, and the individual setting information is the lesion information. It is preferable that the lesion information is a size of the lesion or a type of the lesion.

It is preferable that the notification execution unit performs at least one of an instruction for a screen display output, a sound output instruction, or a vibration output instruction. It is preferable that the screen display output is an image and/or character information.

It is preferable that the notification execution unit performs a screen display output indicating association between the use-notification setting information and the notification according to an instruction from the user.

It is preferable that the notification setting information includes at least one instruction of an instruction for a screen display output, a sound output instruction, or a vibration output instruction performed by the notification execution unit, and the instruction is selected by the user.

It is preferable that the medical image processing device is connected to a medical service support apparatus including an information storage unit in which the patient information and/or diagnosis information is preserved, and the notification setting information selection unit selects the use-notification setting information by using the patient information and/or the diagnosis information read from the information storage unit as the individual setting information.

It is preferable that the diagnosis information includes at least one of user information, part information, procedure information, or lesion information.

It is preferable that an individual setting information input unit that inputs the individual setting information is further provided.

According to the invention, it is possible to prevent overlooking of a lesion or the like by easily performing setting and changing of a notification method for notifying a user in a case where a region of interest as a target for diagnosis is detected from a medical image.

DESCRIPTION OF THE PREFERRED EMBODIMENTS

First Embodiment

Figure 1:
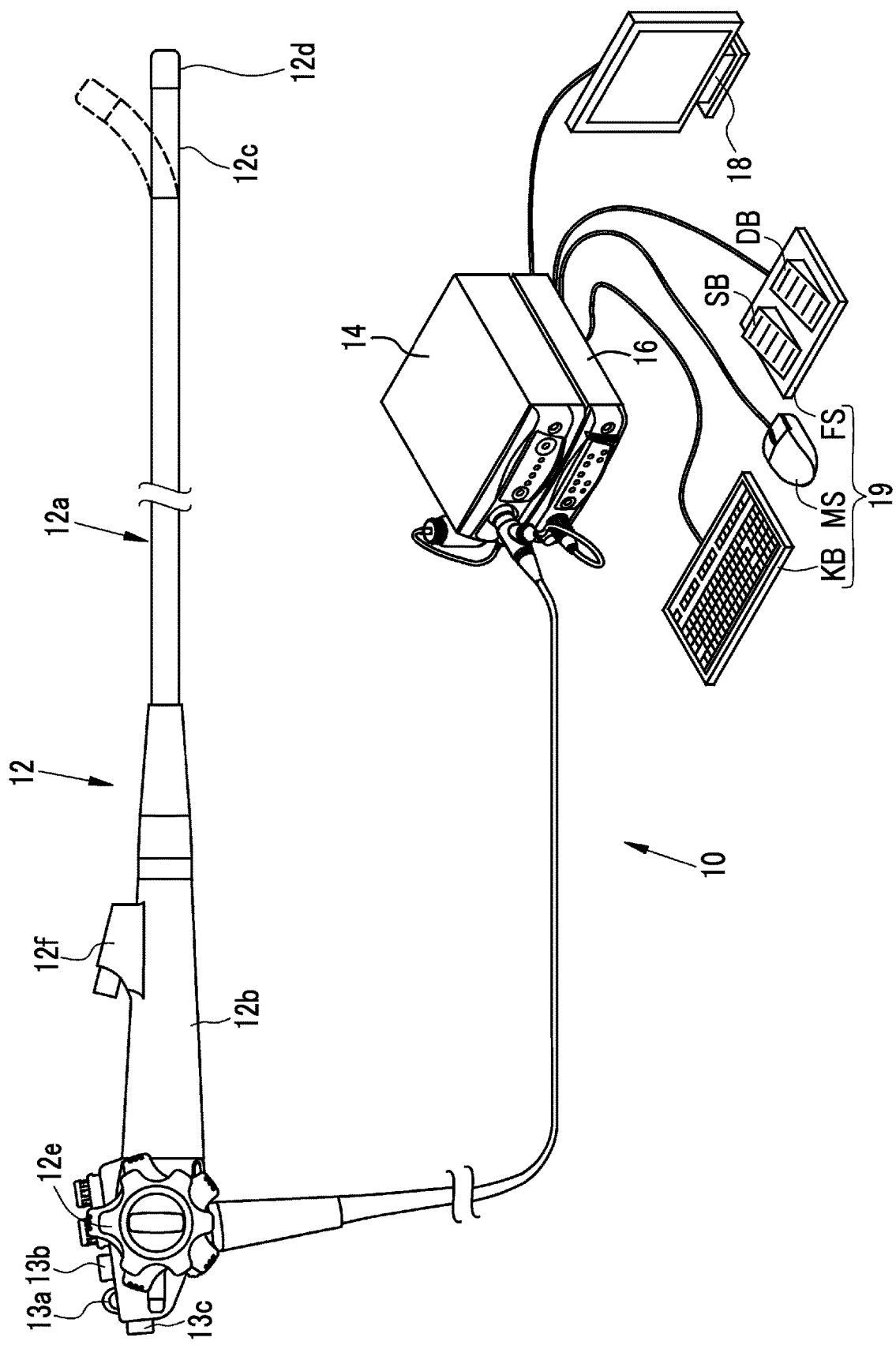
FIG. 1 is an external view of an endoscope system.

As illustrated in FIG. 1, an endoscope system 10 comprises an endoscope 12, a light source device 14, a processor device 16, a monitor 18, and a user interface 19. The endoscope 12 irradiates a subject as an observation target with illumination light, and images the subject irradiated with the illumination light. The light source device 14 generates illumination light to be emitted to the subject. The processor device 16 performs system control of the endoscope system 10, image processing, and the like. The monitor 18 is a display unit that displays an image output from the processor device 16. The user interface 19 is an input device, such as a keyboard, for performing a setting input or the like with respect to the processor device 16 and the like.

The endoscope 12 has an insertion part 12a that is to be inserted into an object to be examined, an operation part 12b provided in a proximal end portion of the insertion part 12a, and a bendable part 12c and a distal end part 12d that are provided on the distal end side of the insertion part 12a. The bendable part 12c is bent by operating an angle knob 12e of the operation part 12b. The distal end part 12d is directed in a desired direction by the bending of the bendable part 12c. A spray port (not illustrated) for spraying air, water, or the like toward the subject is provided in the distal end part 12d.

In addition to the angle knob 12e, a zoom operation part 13a is provided in the operation part 12b. The subject can be imaged in an enlarged or reduced manner by operating the zoom operation part 13a. A forceps channel (not illustrated) for inserting a treatment tool and the like is provided from the insertion part 12a to the distal end part 12d. The treatment tool is inserted into the forceps channel from a forceps inlet 12f.

Further, a scope switch 13b as one of the user interface 19 is provided to the operation part 12b. The scope switch 13b performs an input such as a setting instruction with respect to the processor device 16 or the like by remote access.

Figure 2:
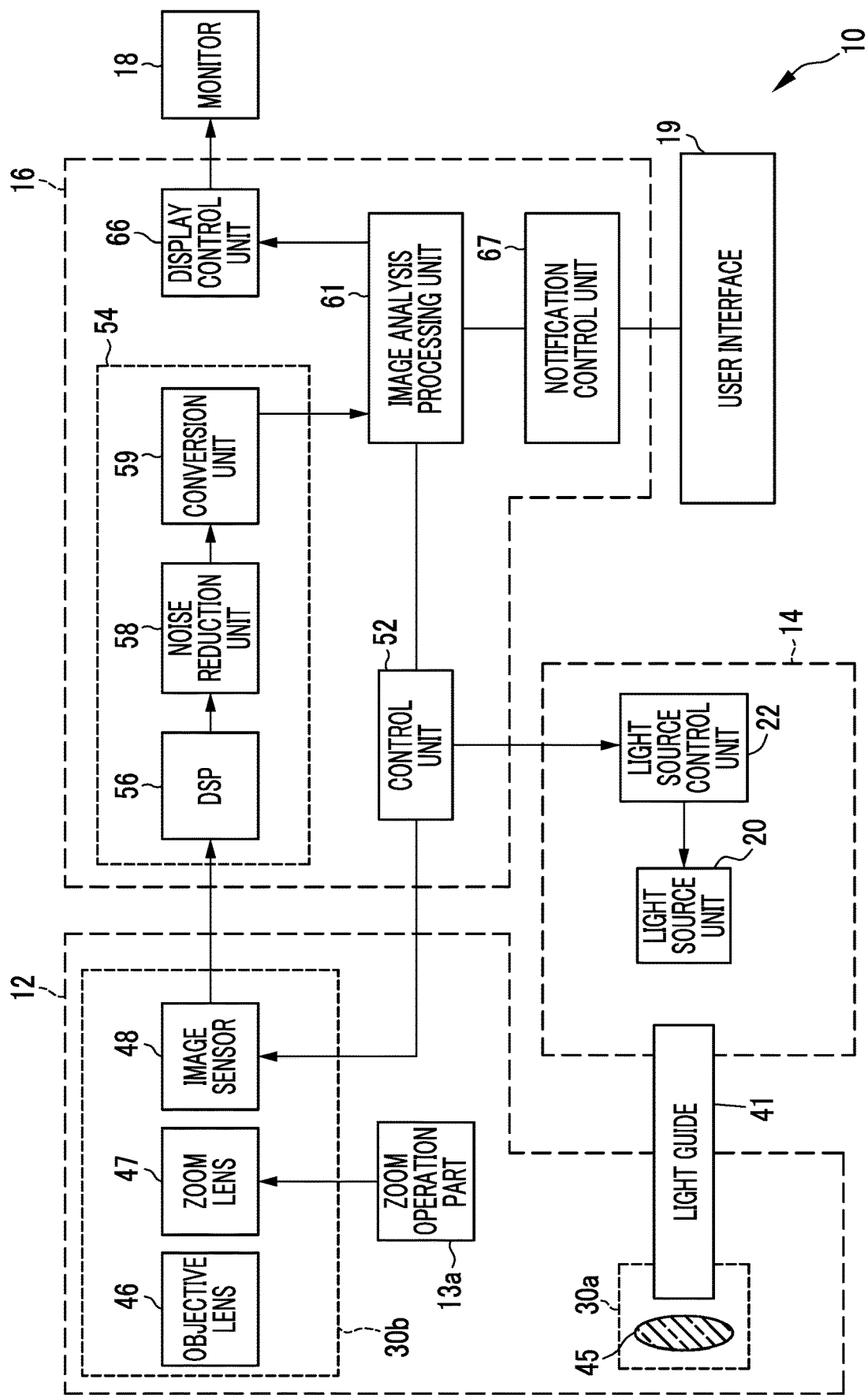
FIG. 2 is a block diagram of the endoscope system.

As illustrated in FIG. 2, the light source device 14 comprises a light source unit 20 and a light source control unit 22. The light source unit 20 emits illumination light for illuminating the subject. The light source unit 20 comprises one or a plurality of light sources. The light source control unit 22 controls the driving of the light source unit 20. The light source control unit 22 independently controls the timing of turning on or off the light sources constituting the light source unit 20, and the light emission amount or the like at the time of lighting. As a result, the light source unit 20 can emit a plurality of kinds of rays of illumination light with different light emission amounts and different light emission timings.

The illumination light emitted from the light source unit 20 is incident on a light guide 41. The light guide 41 is built in the endoscope 12 and a universal cord, and propagates illumination light to the distal end part 12d of the endoscope 12. The universal cord is a cord for connecting the endoscope 12 to the light source device 14 and the processor device 16. It is possible to use a multi-mode fiber as the light guide 41. As an example, it is possible to use a small-diameter fiber cable of which a core diameter is 105 μm, a cladding diameter is 125 μm, and a diameter including a protective layer as an outer skin is φ0.3 mm to φ0.5 mm.

An illumination optical system 30a and an imaging optical system 30b are provided in the distal end part 12d of the endoscope 12. The illumination optical system 30a has an illumination lens 45, and illumination light is emitted toward the subject through the illumination lens 45. The imaging optical system 30b has an objective lens 46, a zoom lens 47, and an image sensor 48. The image sensor 48 images the subject using reflected light or the like (including scattered light, fluorescence emitted from the subject, fluorescence due to medicine administered to the subject, and the like in addition to the reflected light) of the illumination light that returns from the subject through the objective lens 46 and the zoom lens 47. The zoom lens 47 is moved by operating the zoom operation part 13a, thereby enlarging or reducing the subject to be imaged by using the image sensor 48.

The image sensor 48 is, for example, a color sensor having primary color system color filters, and comprises three kinds of pixels of a blue pixel (B pixel) having a blue color filter, a green pixel (G pixel) having a green color filter, and a red pixel (R pixel) having a red color filter. The blue color filter mainly transmits violet to blue light. The green color filter mainly transmits green light. The red color filter mainly transmits red light. In a case where the subject is imaged using the primary color system image sensor 48 as described above, three types of images of a blue image (B image) obtained from the B pixel, a green image (G image) obtained from the G pixel, and a red image (R image) obtained from the R pixel can be simultaneously obtained at maximum.

As the image sensor 48, it is possible to use a charge coupled device (CCD) sensor or a complementary metal oxide semiconductor (CMOS) sensor. Although the image sensor 48 of the embodiment is a primary color system color sensor, it is also possible to use a complementary color system color sensor. For example, the complementary color system color sensor has a cyan pixel in which a cyan color filter is provided, a magenta pixel in which a magenta color filter is provided, a yellow pixel in which a yellow color filter is provided, and a green pixel in which a green color filter is provided. Images obtained from the pixels of the respective colors in case of using the complementary color system color sensor can be converted into the B image, the G image, and the R image by performing complementary color-primary color conversion. Instead of the color sensor, a monochrome sensor in which no color filter is provided can be used as the image sensor 48. In this case, it is possible to obtain images of the respective colors by sequentially imaging the subject using illumination light of respective colors such as BGR.

The processor device 16 includes a control unit 52, an image acquisition unit 54, an image analysis processing unit 61, a display control unit 66, and a notification control unit 67. The control unit 52 performs overall control of the endoscope system 10, such as synchronization control of irradiation timing of illumination light and imaging timing. In a case where various settings are input using the user interface 19 or the like, the control unit 52 inputs the settings to each unit of the endoscope system 10, such as the light source control unit 22, the image sensor 48, or the image analysis processing unit 61.

The image acquisition unit 54 acquires an image in which the subject is imaged, from the image sensor 48. Since the image acquired by the image acquisition unit 54 is an image obtained by a medical apparatus, such as the endoscope 12, the image is referred to as a medical image. The image acquisition unit 54 includes a digital signal processor (DSP) 56, a noise reduction unit 58, and a conversion unit 59, and performs various kinds of processing on the acquired medical image using these as necessary. The DSP 56 performs various kinds of processing, such as defect correction processing, offset processing, gain correction processing, linear matrix processing, gamma conversion processing, demosaicing processing, and YC conversion processing, on the acquired medical image as necessary.

The defect correction processing is processing for correcting the pixel value of each pixel corresponding to the defective pixel of the image sensor 48. The offset processing is processing for setting an accurate zero level by reducing a dark current component from the image subjected to the defect correction processing. The gain correction processing is processing for adjusting a signal level of each image by multiplying the image subjected to the offset processing by the gain. The linear matrix processing is processing for improving the color reproducibility of the image subjected to the offset processing, and the gamma conversion processing is processing for adjusting the brightness or the saturation of the image after the linear matrix processing.

In a case where the image sensor 48 is a color sensor, demosaicing processing is performed. The demosaicing processing (also referred to as isotropic processing or demosaicing) is processing for interpolating the pixel values of missing pixels, and is performed on the image after the gamma conversion processing. The missing pixel is a pixel having no pixel value due to the arrangement of color filters (since pixels of other colors are arranged in the image sensor 48). For example, since the B image is an image obtained by imaging the subject in the B pixel, a pixel at a position corresponding to the G pixel or the R pixel has no pixel value. The demosaicing processing is for generating the pixel values of pixels at the positions of the G and R pixels of the image sensor 48 by interpolating the B image. The YC conversion processing is processing for converting the image after the demosaicing processing into a luminance channel Y, a color difference channel Cb, and a color difference channel Cr.

The noise reduction unit 58 performs noise reduction processing on the luminance channel Y, the color difference channel Cb, and the color difference channel Cr using, for example, a moving average method or a median filter method. The conversion unit 59 reconverts the luminance channel Y, the color difference channel Cb, and the color difference channel Cr after the noise reduction processing into images of the respective colors of BGR.

The image analysis processing unit 61 performs various kinds of image processing on the medical image acquired by the image acquisition unit 54. In the embodiment, in the image analysis processing unit 61, image processing for detecting a region of interest as a region to be noticed is performed on the basis of the feature quantity of the pixels of the medical image, and the region of interest is notified to the user. The image analysis processing unit 61 transmits the medical image to the display control unit 66. The image analysis processing unit 61 will be described below in detail.

The display control unit 66 converts the medical image transmitted from the image analysis processing unit 61 or an instruction for a screen display output performed by a notification execution unit 78, which will be described below, into a format suitable for display on the monitor 18, and outputs the conversion result to the monitor 18. In this manner, on the monitor 18, at least the medical image is displayed, and in a case where a notification is executed by the notification control unit 67 which will be described below, a notification is performed by being displayed together with the medical image.

The notification control unit 67 performs settings or the like of notification setting information relating to a notification performed with respect to the user, according to the settings of the notification method received from the user interface 19 or the like. Further, the notification is executed to the user using a display or a sound by controlling the monitor 18 or the like on the basis of the notification setting information. The notification control unit 67 will be described below in detail.

In the specification, the "notification" refers to an output performed in a method that the user can recognize, such as a sound, vibration, or a screen display. Further, the "notification setting" refers to setting of the notification content regarding which method the notification is performed in, and the "notification setting information" refers to data for setting the notification setting to the notification control unit 67.

Figure 3:
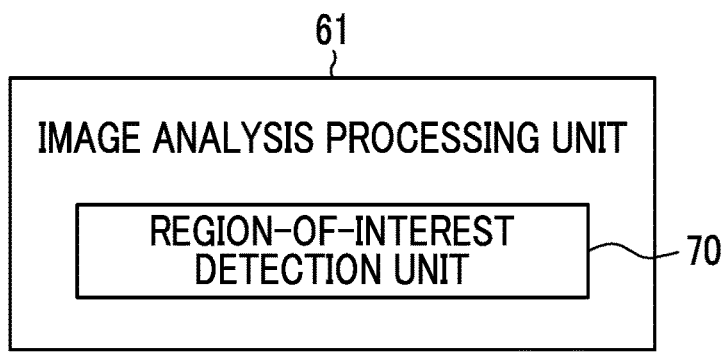
FIG. 3 is a block diagram illustrating an image analysis processing unit of a first embodiment.

As illustrated in FIG. 3, in this example, the image analysis processing unit 61 comprises a region-of-interest detection unit 70. The region-of-interest detection unit 70 detects a region of interest to be noticed as a target for inspection or diagnosis from the medical image. In the region-of-interest detection unit 70, a region of interest is detected on the basis of, for example, a feature quantity obtained by color information and the gradient of the pixel values of the medical image, in addition to performing convolutional neural network on the medical image. The gradient of the pixel values or the like is changed depending on, for example, the shape of the subject (global undulations of a mucous membrane or local depressions or bumps), color (color such as whitening due to inflammation, bleeding, redness, or atrophy), a feature of a tissue (thickness, depth, or density of a blood vessel, or a combination thereof), or a feature of a structure (pit pattern or the like).

Further, the region of interest detected by the region-of-interest detection unit 70 is a region including a lesion area represented by a cancer, a benign tumor area, an inflammation area (including a portion with changes such as bleeding or atrophy in addition to a so-called inflammation), a cauterization scar due to heating or a marking area marked by coloring with a coloring agent, a fluorescent agent, or the like, or a biopsy area where biopsy inspection (so called biopsy) is performed. That is, a region including a lesion, a region having a possibility of a lesion, a region where any treatment such as a biopsy is performed, a treatment tool such as clips or forceps, a region which is required to be observed in detail regardless of a possibility of a lesion, such as a dark region (back of folds, a region where observation light is difficult to reach due to the depth of the lumen), or the like can be a region of interest. In the endoscope system 10, the region-of-interest detection unit 70 detects a region including at least one of a lesion area, a benign tumor area, an inflammation area, a marking area, or a biopsy area, as the region of interest.

Figure 4:
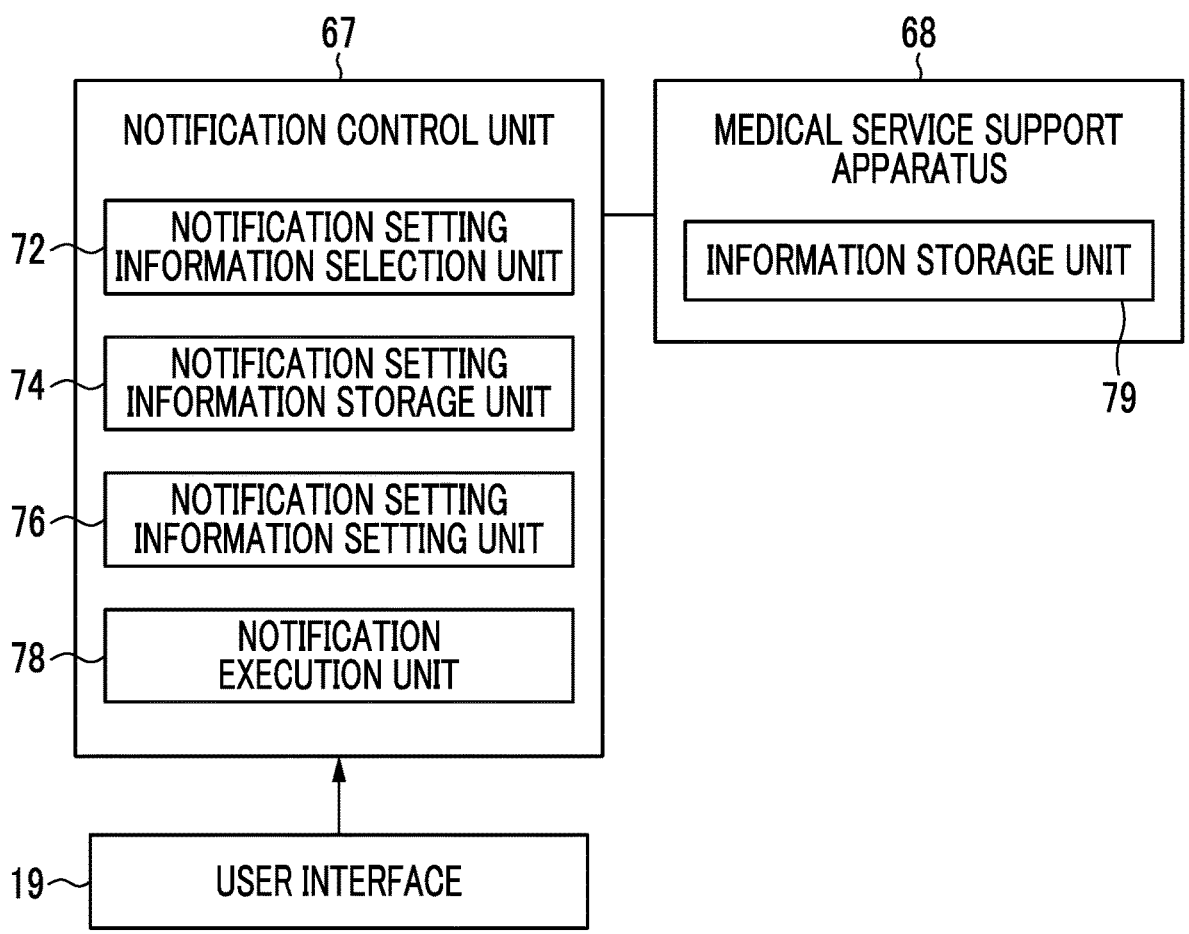
FIG. 4 is a block diagram illustrating a notification control unit, a user interface, and a medical service support apparatus.

As illustrated in FIG. 4, the notification control unit 67 comprises a notification setting information selection unit 72, a notification setting information storage unit 74, a notification setting information setting unit 76, and the notification execution unit 78. The notification setting information setting unit 76 creates notification setting information and transmits the notification setting information to the notification execution unit 78 and the notification setting information storage unit 74. The notification execution unit 78 issues a notification output instruction according to the notification setting information to execute a notification, and the notification setting information storage unit 74 preserves the notification setting information. Next, the notification setting information selection unit 72 selects the notification setting information preserved in the notification setting information storage unit 74 by performing search using individual setting information, and transmits the notification setting information as use-notification setting information to the notification execution unit 78, and the notification is executed. The individual setting information is associated with the notification setting information, but is preserved as information different from the notification setting information in the notification setting information storage unit 74 together with the notification setting information. Since the notification control unit 67 has such a configuration, for example, in a case where the device is used by a plurality of users and each user desires to arbitrarily change the notification setting, it is possible to easily set the notification setting information of the notification method which is described in detail in the notification setting information by each user. Further, even in case of the same user, since various pieces of individual setting information are preserved by being associated with the notification setting information, it is possible to perform an appropriate notification of which the setting is changed for each patient, each part, or each procedure by easy change. In this manner, the notification setting information is linked with the individual setting information which is configured to be searchable, and is selected by searching for the individual setting information. In this example, as the individual setting information, four items of "user information", "patient information", "part information", and "procedure information" are used. It becomes easy to select the notification setting information using the individual setting information by associating the notification setting information with at least one piece of the individual setting information. In some cases, one piece of notification setting information can be associated with two or more of a plurality of pieces of individual setting information, and two or more of a plurality of pieces of notification setting information can be associated with one piece of individual setting information.

With the individual setting information input from the user interface 19 as a condition, the notification setting information selection unit 72 selects notification setting information matching the condition, from the notification setting information preserved in the notification setting information storage unit 74, and transmits the selected notification setting information as the use-notification setting information to the notification execution unit 78. In this example, as the user interface 19, a keyboard (KB), a mouse (MS), and a foot switch (FS) (refer to FIG. 1) are used. The user interface 19 is an example of an individual setting information input unit.

Among the individual setting information, the user information is information relating to a user such as a doctor, and, for example, in case of a doctor, the user information may be a post and affiliation, a position such as a resident, or a specialized field, and may be information for identifying individuals, such as a name, an identification (ID), a password, a doctor's license number, a doctor's electronic signature, a doctor's image, and doctor's biometric information such as a fingerprint. Further, the patient information is information relating to a patient, may be information for identifying a patient, such as a patient ID, a password, an address, a name, age, date of birth, gender, and a patient's image, patient's biometric information such as a fingerprint, a telephone number, and a health insurance card number, and may be a medical record number, a disease name, a blood type, a type of inspection, an inspection date, an inspection time, a reception number, a used inspection device ID, an inspection result such as an inspection image, a prescription drug, a prescription number, information relating to wearing equipment, a doctor in charge, a nurse in charge, an inspection technician, a medical history, information relating to hospitalization, information relating to consultation and medical history such as a receipt number, an inspection date, and an operation date. For these, a common ID or the like with the diagnosis support apparatus and/or a medical service support apparatus 68 in the hospital may be used. Further, the part information is information relating to which part the subject of which the medical image is acquired is, and specifically, stomach, large intestine, names of other parts, and the state of these subjects are exemplified. The procedure information is information of a procedure performed after the medical image is acquired, and screening, endoscopic submucosal dissection (ESD), endoscopic polypectomy (polypectomy), and the like can be arbitrarily set. In this example, as the individual setting information, the four items described above are used, but without being limited thereto, any item can be set.

By an input of individual setting information, the notification setting information selection unit 72 searches for notification setting information associated with the individual setting information from the notification setting information storage unit 74. There may be a plurality of pieces of corresponding notification setting information depending on the search results, and in such a case, the user selects the notification setting information that the user desires to use by the user interface 19. For example, it is possible to select the notification setting information that the user desires to use from a list of notification setting information displayed on the monitor 18. In a case where the notification setting information is selected, the notification setting information selection unit 72 transmits the notification setting information as the use-notification setting information to the notification execution unit 78. Accordingly, the notification setting information includes information on at least one instruction of an instruction for a screen display output, a sound output instruction, or a vibration output instruction that is selected by the user and is to be performed by the notification execution unit.

Figure 5:
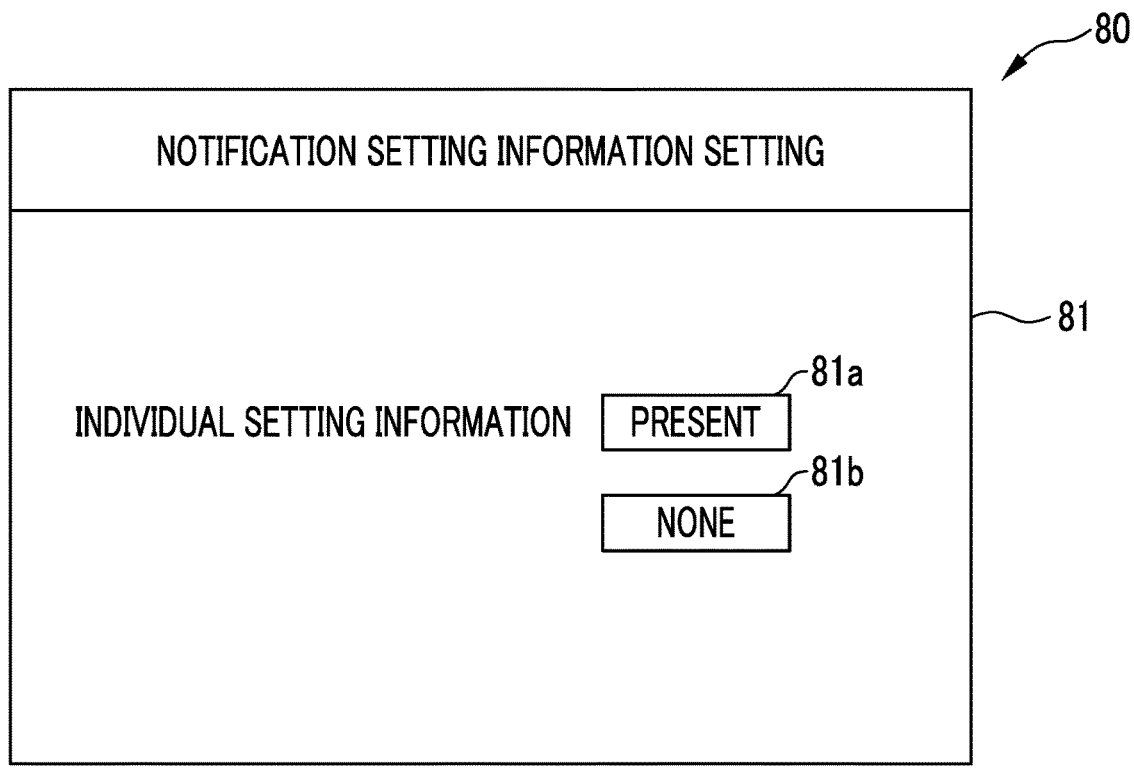
FIG. 5 is an image diagram illustrating a notification setting information setting screen (initial screen) in a monitor.
Figure 6:
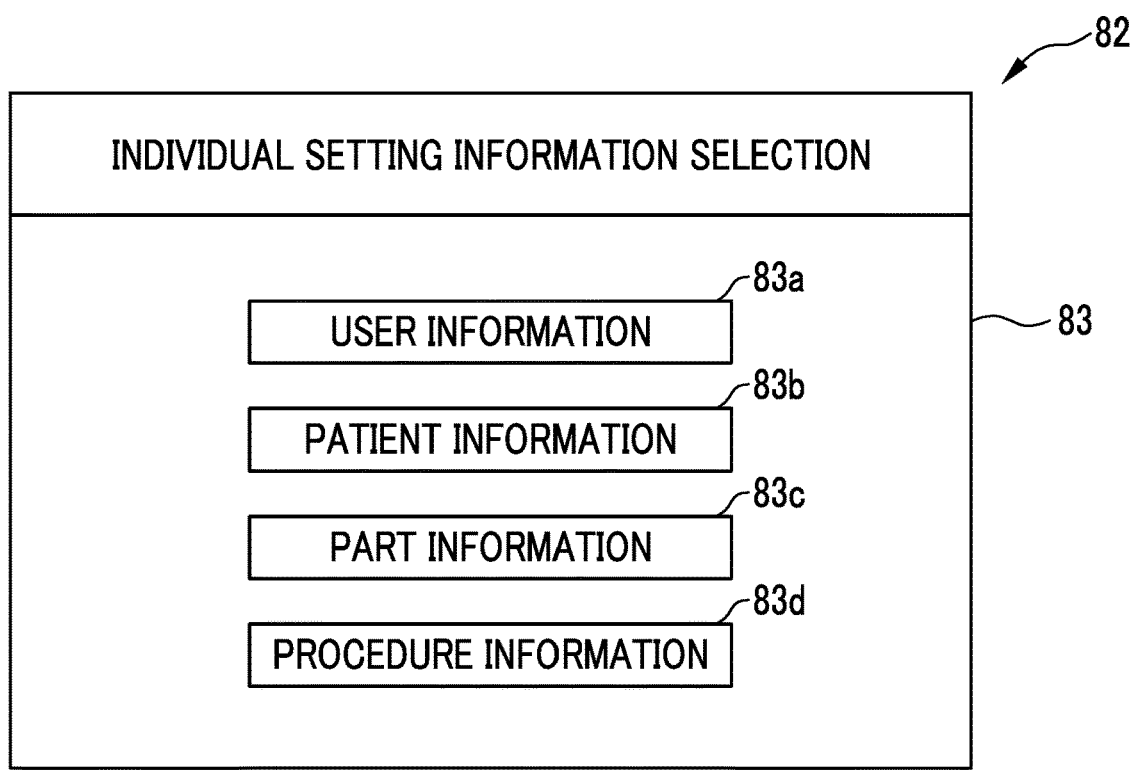
FIG. 6 is an image diagram illustrating an individual setting information selection screen in the monitor.

In this example, the procedure of selecting the notification setting information by the notification setting information selection unit 72 is as follows. As illustrated in FIG. 5, initially, a notification setting information setting screen (initial screen) 80 including a selection region 81 is displayed on the monitor 18. The user who desires to call and use the notification setting information from the notification setting information storage unit 74 selects a selection button 81a of "present" of the selection region 81. Then, as illustrated in FIG. 6, in an individual setting information selection screen 82 including an individual setting information selection region 83, the type of individual setting information with which the notification setting information the user desires to use currently is associated, by individual setting information selection buttons 83a to 83d. By an input of information required for each type of individual setting information, the notification setting information selected by the user is selected from the notification setting information preserved in the notification setting information storage unit 74, and is set as the use-notification setting information.

Figure 7:
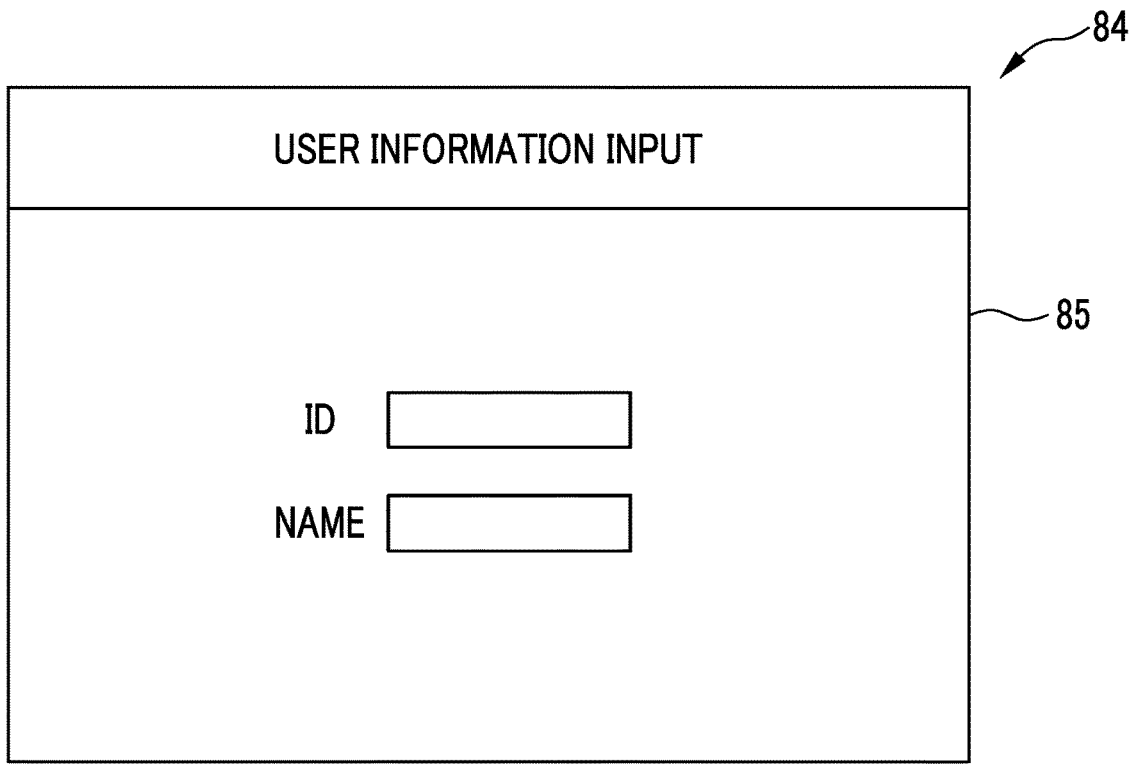
FIG. 7 is an image diagram illustrating a user information input screen in the monitor.
Figure 8:
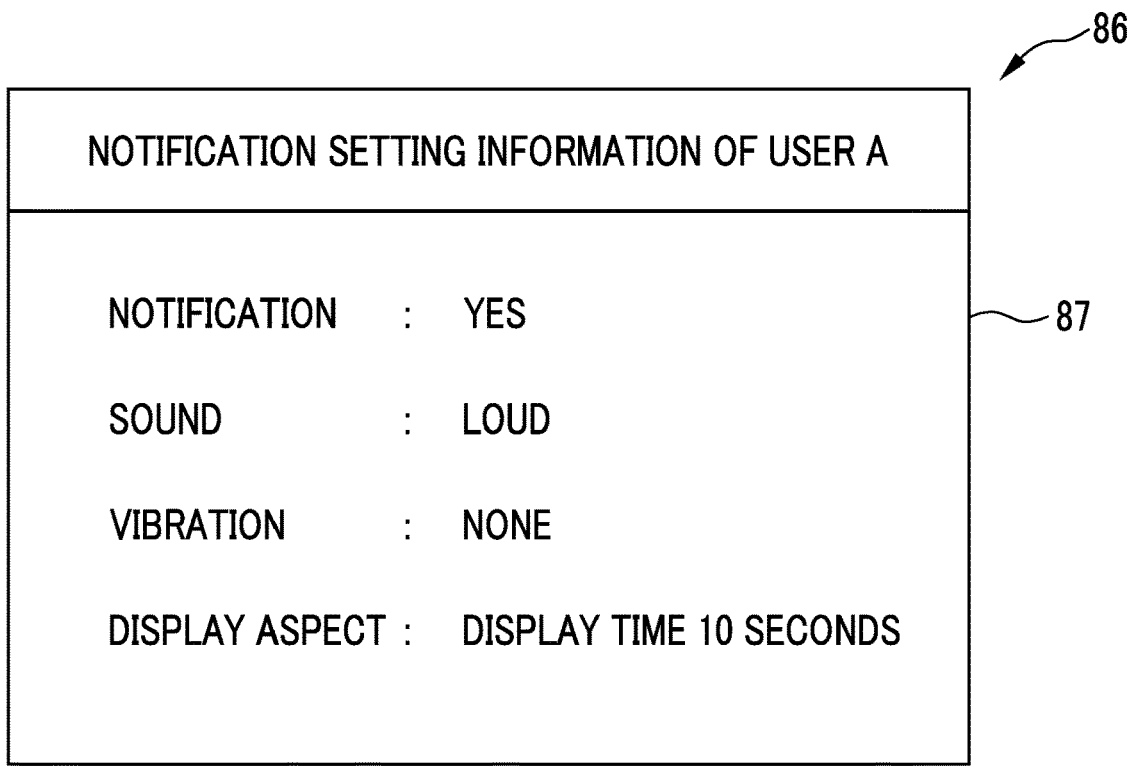
FIG. 8 is an image diagram illustrating a notification setting information display screen in the monitor.

In the individual setting information selection screen 82, in a case where the user information is selected as the type of individual setting information, as illustrated in FIG. 7, a user information input screen 84 including a user information input region 85 is displayed. The user information input region 85 includes a region where the user's ID or the user's name as the individual setting information is input. The user inputs the user's ID or the user's name as the individual setting information associated with the notification setting information that the user desires to use, using the user interface 19. In a case where notification setting information associated with the user's ID or the user's name as the input individual setting information is present in the notification setting information storage unit 74, as illustrated in FIG. 8, the details of the selected notification setting information can be checked by a notification setting information display screen 86 including a notification setting information detail display region 87. The notification setting information display screen 86 is displayed on the monitor 18. In this example, in the notification setting information detail display region 87, in case of the individual setting information of a user A, "notification: yes" is displayed, which represents that a notification is to be executed. Further, "sound: loud" is displayed, which represents that a notification is to be executed by a sound output and the volume is high level. Further, "vibration: none" is displayed, which represents that a notification is not to be executed by a vibration output. Further, "display aspect: display time 10 seconds" is displayed, which represents that a notification is to be executed by a screen display output and the display time is 10 seconds.

Figure 9:
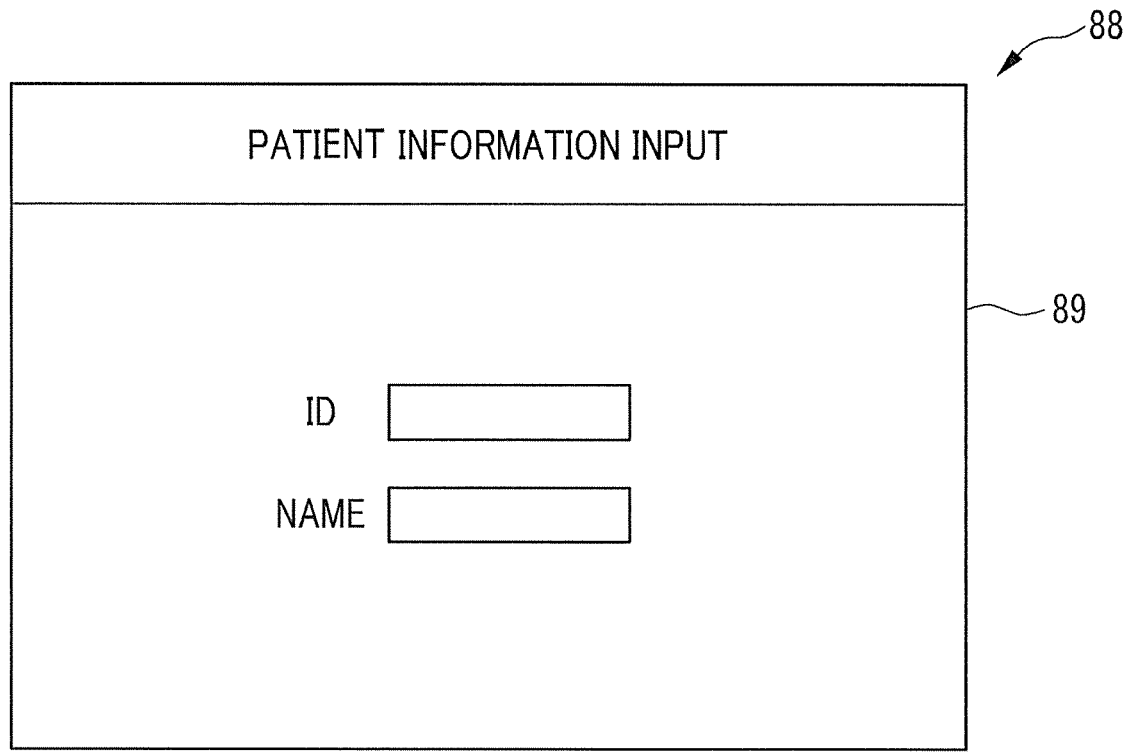
FIG. 9 is an image diagram illustrating a patient information input screen in the monitor.
Figure 10:
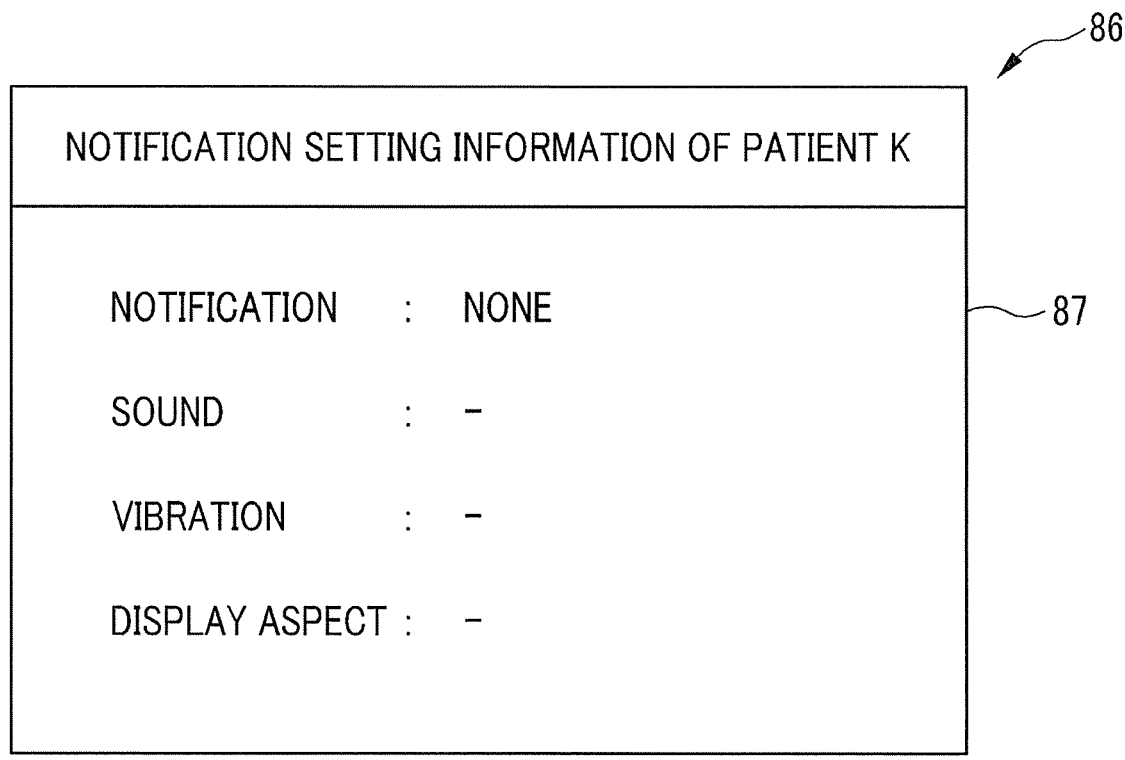
FIG. 10 is an image diagram illustrating a notification setting information display screen in the monitor.

Similarly, in the individual setting information selection screen 82 (refer to FIG. 6), in a case where the patient information is selected as the type of individual setting information, as illustrated in FIG. 9, a patient information input screen 88 including a patient information input region 89 is displayed on the monitor 18. The patient information input region 89 includes a region where the patient's ID or the patient's name as the individual setting information is input. The user inputs the patient's ID or the patient's name as the individual setting information associated with the notification setting information that the user desires to use, using the user interface 19. In a case where notification setting information associated with the patient's ID or the patient's name as the input individual setting information is present in the notification setting information storage unit 74, as illustrated in FIG. 10, the details of the selected notification setting information can be checked by the notification setting information display screen 86 including the notification setting information detail display region 87. In this example, in the notification setting information detail display region 87, in case of the individual setting information of a patient K, "notification: none" is displayed, which represents that a notification is not executed. Since the notification is not executed, the regions of "sound", "vibration", and "display aspect" are displayed with a symbol "-" meaning that there is no notification setting information relating thereto.

Figure 11:
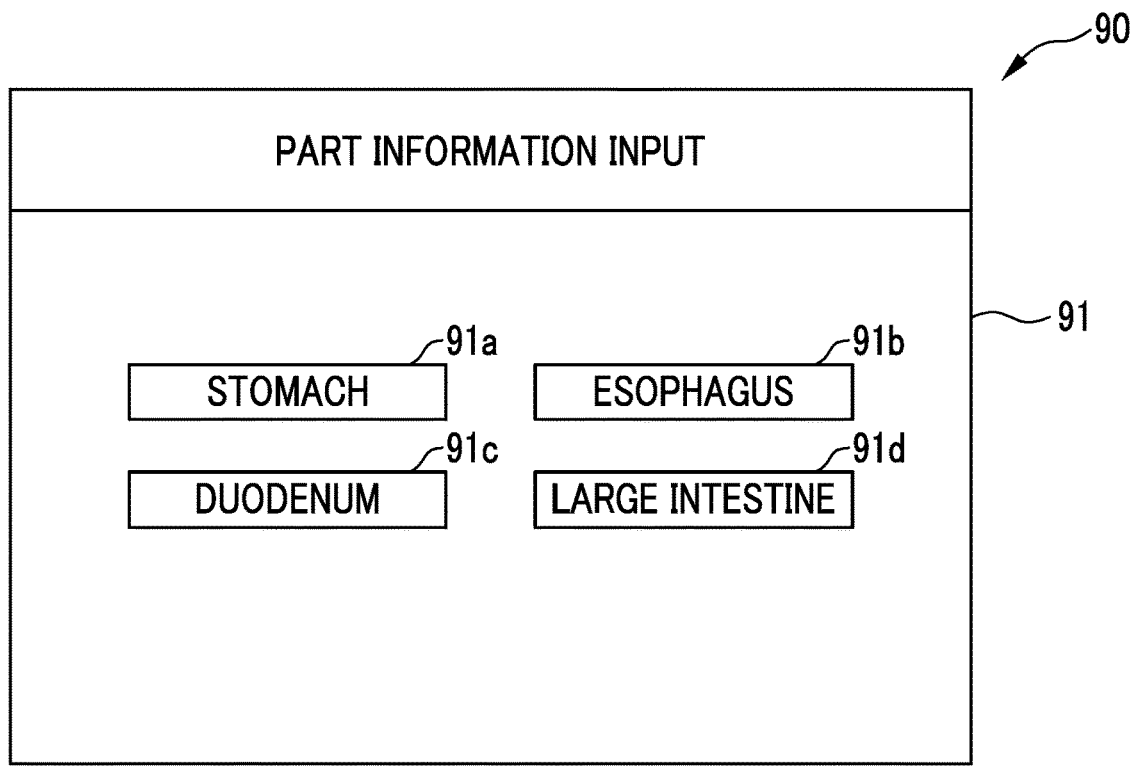
FIG. 11 is an image diagram illustrating a part information input screen in the monitor.
Figure 12:
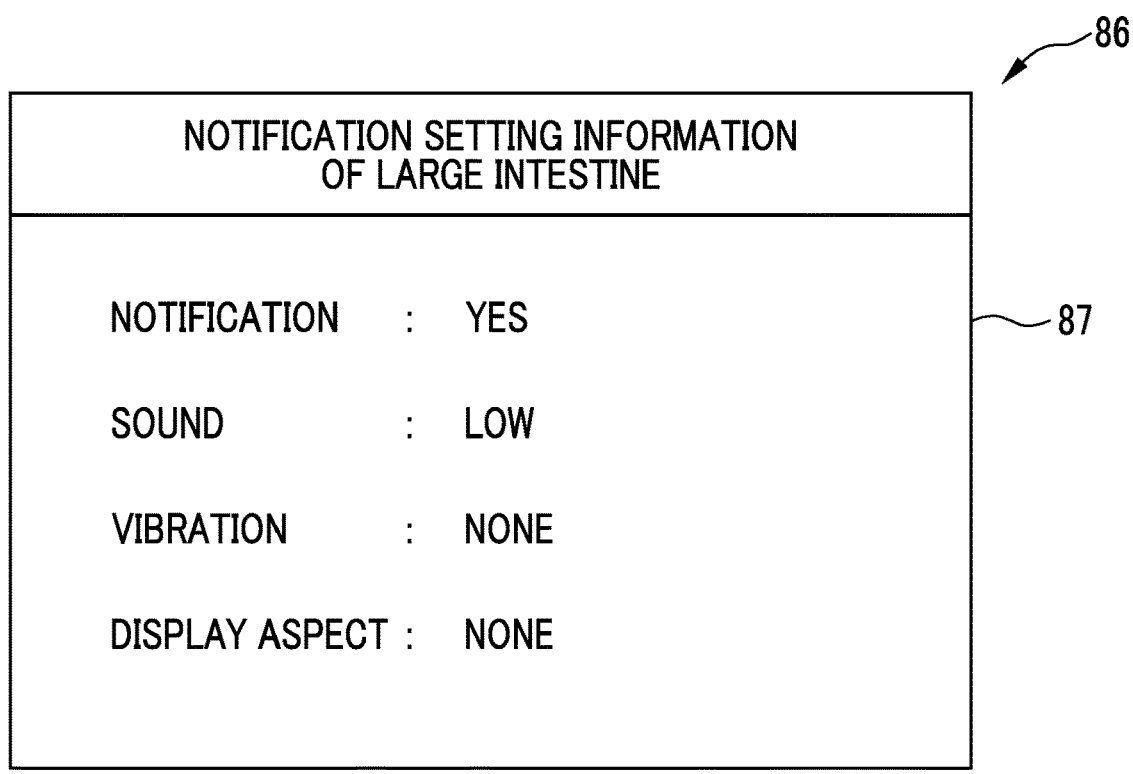
FIG. 12 is an image diagram illustrating a notification setting information display screen in the monitor.

In the individual setting information selection screen 82 (refer to FIG. 6), in a case where the part information is selected as the type of individual setting information, as illustrated in FIG. 11, a part information input screen 90 including a part information input region 91 is displayed on the monitor 18. The part information input region 91 includes a region where the part as the individual setting information is selected by part information selection buttons 91a to 91d. The user inputs the part information selection button corresponding to the part as the individual setting information associated with the notification setting information that the user desires to use, using the user interface 19. In a case where notification setting information associated with the part as the input individual setting information is present in the notification setting information storage unit 74, as illustrated in FIG. 12, the details of the selected notification setting information can be checked by the notification setting information display screen 86 including the notification setting information detail display region 87. In this example, in the notification setting information detail display region 87, in case of the individual setting information of large intestine, "notification: yes" is displayed, which represents that a notification is to be executed. Further, "sound: low" is displayed, which represents that a notification is to be executed by a sound output and the volume is low level. Further, "vibration: none" is displayed, which represents that a notification is not to be executed by a vibration output. Further, "display aspect: none" is displayed, which represents that a notification is not to be executed by a screen display output.

Figure 13:
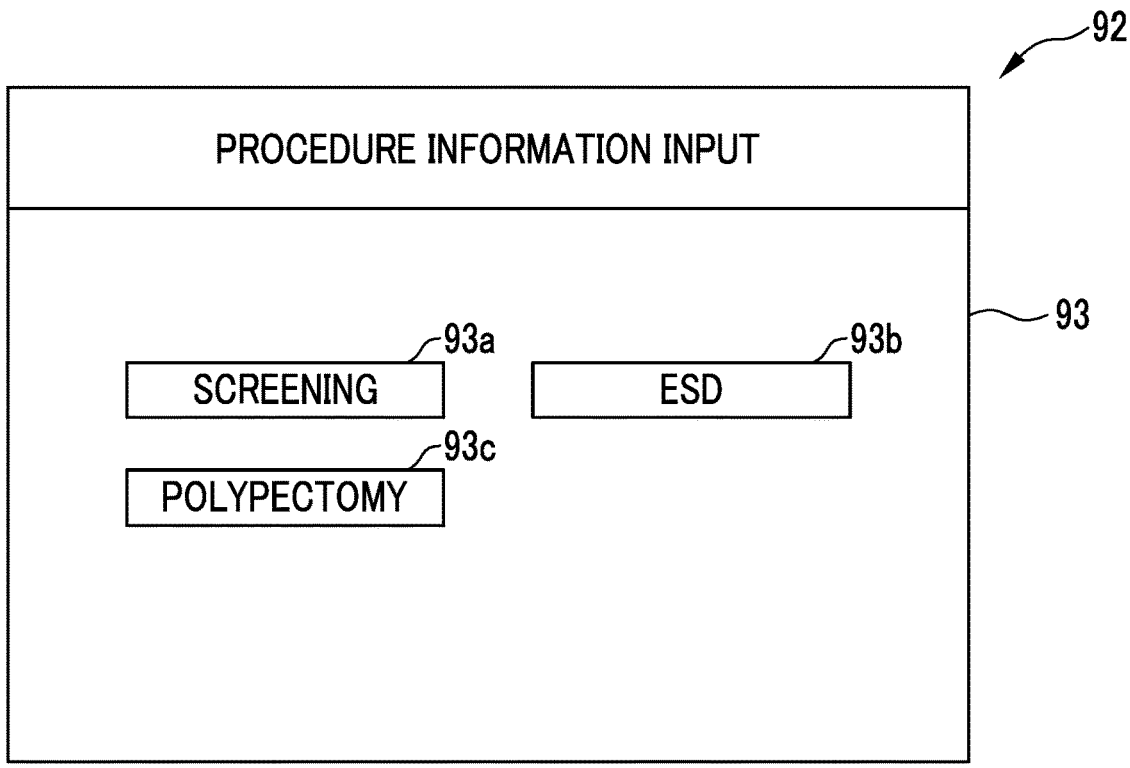
FIG. 13 is an image diagram illustrating a procedure information input screen in the monitor.
Figure 14:
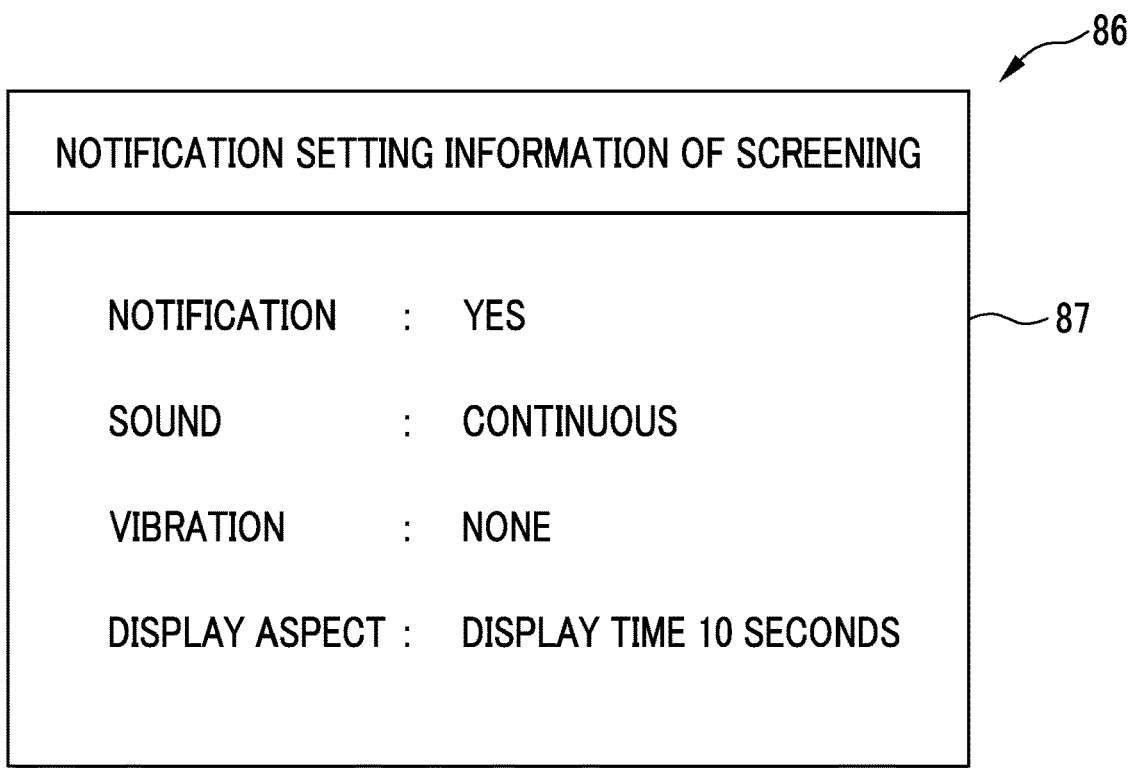
FIG. 14 is an image diagram illustrating a notification setting information display screen in the monitor.

Similarly, in the individual setting information selection screen 82 (refer to FIG. 6), in a case where the procedure information is selected as the type of individual setting information, as illustrated in FIG. 13, a procedure information input screen 92 including a procedure information input region 93 is displayed on the monitor 18. The procedure information input region 93 includes a region where the procedure as the individual setting information is selected by a button. The user inputs procedure information selection buttons 93a to 93c corresponding to the procedure as the individual setting information associated with the notification setting information that the user desires to use, using the user interface 19. In a case where notification setting information associated with the procedure as the input individual setting information is present in the notification setting information storage unit 74, as illustrated in FIG. 14, the details of the selected notification setting information can be checked by the notification setting information display screen 86 including the notification setting information detail display region 87. In this example, in the notification setting information detail display region 87, in case of screening, "notification: yes" is displayed, which represents that a notification is to be executed. Further, "sound: continuous" is displayed, which represents that a notification is to be executed by a sound output and the pattern is a continuous sound. Further, "vibration: none" is displayed, which represents that a notification is not to be executed by a vibration output. Further, "display aspect: display time 10 seconds" is displayed, which represents that a notification is to be executed by a screen display output and the display time is 10 seconds.

In a case where the individual setting information is not input so that the region is left blank, notification setting information having initial setting including normally used notification setting is set. In a case where a device is connected to the medical service support apparatus 68 including an information storage unit 79 in which patient information and/or diagnosis information is preserved, the notification setting information selection unit 72 can select the use-notification setting information by using the patient information and/or the diagnosis information read from the information storage unit 79 as the individual setting information (refer to 4). For example, by using the patient information and/or the diagnosis information acquired from the medical service support apparatus 68 other than the user interface 19 as the individual setting information, the individual setting information can be input from other than the user interface 19, and the use-notification setting information can be set to the notification setting information setting unit 76. Further, as described below, it is possible to input the individual setting information using the endoscope system 10.

The information preserved in the information storage unit 79 includes, for example, information described in the medical record or the like, and includes the patient information, the diagnosis information, and the like. The diagnosis information includes at least one of the user information, the part information, the procedure information, or the lesion information, and further includes endoscope order information and endoscopy information. The endoscope order information includes reservation information required for inspection, such as the patient's name or the patient's ID, the inspection content, and the treatment content, which is input from the user in advance to the medical service support apparatus 68 for performing the inspection of a specific patient. Further, for the endoscope order information, the information can be directly input from the endoscope system 10, and the information can be transmitted from the medical service support apparatus 68 to the endoscope system 10. For example, in case of a patient who had been subjected to the inspection in the past, the endoscopy information includes the content of the lesion, the biopsy content, the treatment content, and the like in addition to the endoscope order information, and also includes diagnosis progress information or the like.

In a case where the image analysis processing unit 61 is configured to be capable of detecting a treatment tool used in the procedure in addition to detecting a region of interest and determining the content of the lesion, when the treatment tool is detected, the procedure using the treatment tool can be used as the procedure information. In this case, the use-notification setting information can be selected by using the procedure information as the individual setting information.

Regarding the input, as long as the individual setting information can be selected, input means is not limited. However, it is preferable that the input means allows the user to perform an input as easy as possible such that the notification method can be appropriately modified in a case where the user desires a change during the use of the endoscope 12, for example. Accordingly, in addition to the keyboard KB and the mouse MS as the user interface 19, for example, in a case where each input region on the screen is configured such that a menu list is displayed using a pull-down button and desired one is to be selected from the menu list, it is possible to use a touch input of the monitor 18, the scope switch 13b (refer to FIG. 1) of the operation part 12b of the endoscope 12, a switching switch SB and a confirm switch DB (refer to FIG. 1) of the foot switch FS, a sound input using a microphone, and the like. In a case where the user information is input using the IC tag, the biometric authentication, or the like, it is possible to use input means suitable for each of the IC tag, the biometric authentication, and the like, such as an IC tag reader, and a camera. It is preferable that the notification setting can be changed without a complicated operation by the user during the inspection in particular, by configuring the input means such that the change and modification can be selected by the scope switch 13b or the foot switch FS.

According to the use-notification setting information transmitted from the notification setting information selection unit 72 or the notification setting information setting unit 76, the notification execution unit 78 transmits an instruction of a sound output, a vibration output, a screen output, and the like to sound generation means, vibration generation means, and screen display means, respectively, to execute a notification. The output instruction transmitted from the notification execution unit 78 may be any instruction for outputting something recognizable by a human sensory organ, and a screen display output, a light output, a sound output, and a vibration output are exemplified. Accordingly, as the means for performing an output, the user interface 19 such as the monitor 18 is exemplified. Specifically, in addition to the monitor 18 performing a screen output, a speaker which is provided to the monitor 18 and performs a sound output, a vibrator performing a vibration output are exemplified. Input/output means in which output means is provided to input means may be adopted, the speaker or the vibrator may be provided to the keyboard KB, the mouse MS, the monitor 18, or the foot switch FS as the user interface 19. In addition, by providing a vibrator to the operation part 12b of the endoscope 12 of the endoscope system 10 as the medical image processing device, it is possible for the user to receive various notifications by vibration patterns of the operation part 12b while the user is using the endoscope 12. In addition to the vibrator, a speaker performing a sound output, light emission means for performing a light output, such as an LED, or output means for performing a screen output, such as a display may be provided to the operation part 12b. In a case where output means is provided to the operation part 12b, for example, since the output means is closer to the user as compared with a case in which a notification is performed using a sound from the speaker of the monitor 18, there is no possibility that the notification is mixed with the external sound, and thus it is possible for the user to receive the notification reliably. Further, the connection method of the input/output means may be wired, or may be wireless such as WiFi or IC tag.

Figure 15:
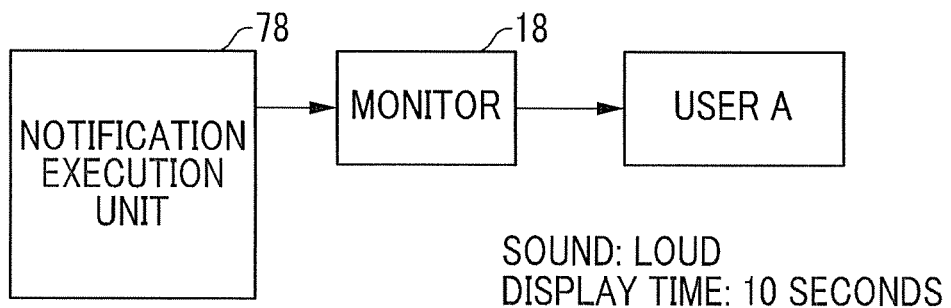
FIG. 15 is an explanatory diagram illustrating that a notification execution unit executes a notification according to notification setting information.

In this example, the notification by the notification execution unit 78 is executed as follows. In a case where the user information is selected as the individual setting information and the notification setting information associated with the user's ID is set (refer to FIGS. 7 and 8), a notification is to be executed according to the notification setting information. That is, as illustrated in FIG. 15, in a case where the user A is used, when a region of interest is detected from the acquired image, a predetermined sound is output with a high volume from the speaker provided to the monitor 18, and a display indicating that a region of interest is detected appears on a part of the screen of the monitor 18. Further, the notification using the screen display for the region of interest is displayed for "10 seconds". In this example, the notification setting information is associated with the user's ID and the notification setting information is set for each user. The set notification setting information is stored in the notification setting information storage unit 74, and can be easily reset by the notification setting information selection unit 72. Accordingly, a device in which detailed settings of how to perform a notification depending on the technique or the degree of proficiency of the user can be easily set, and which is easy to perform diagnosis and is effective in preventing the overlooking can be obtained.

Figure 16:
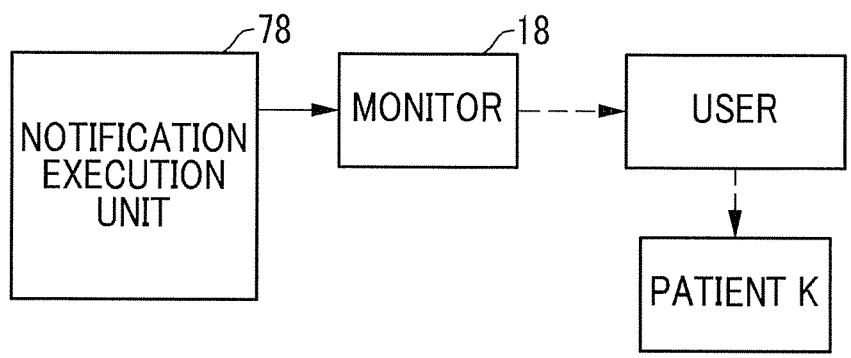
FIG. 16 is an explanatory diagram illustrating that a notification execution unit executes the notification according to notification setting information.

Next, in a case where an image of a person to be examined (patient K) who is a patient for re-inspection and of which the target observation location is predetermined is acquired, notification setting information for not performing a notification for a specific location is set. In this case, the patient information is selected as the individual setting information, an ID of the patient K is input, and the notification setting information associated with the patient K is set (refer to FIGS. 9 and 10). As illustrated in FIG. 16, since the patient K had been subjected to several re-inspection as a follow-up regarding a lesion in a specific location of the stomach, even in a case where a region of interest is detected from an image acquired from the corresponding location, a notification is not performed.

Figure 17:
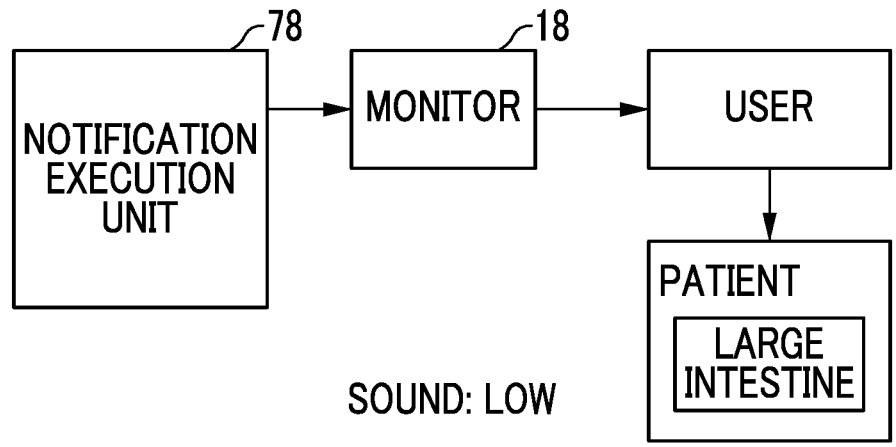
FIG. 17 is an explanatory diagram illustrating that the notification execution unit executes a notification according to notification setting information.

Next, in a case where the part information is selected as the individual setting information and the notification setting information associated with the part name is set (refer to FIGS. 11 and 12), since the large intestine is a part which is relatively easy to recognize a region of interest, a sound output with relatively low volume is set as the notification setting information. Accordingly, as illustrated in FIG. 17, in a case where a region of interest is detected in the large intestine, only a low sound is output from the speaker installed to the monitor 18, and a display indicating that a region of interest is detected does not appear on the screen of the monitor 18.

Figure 18:
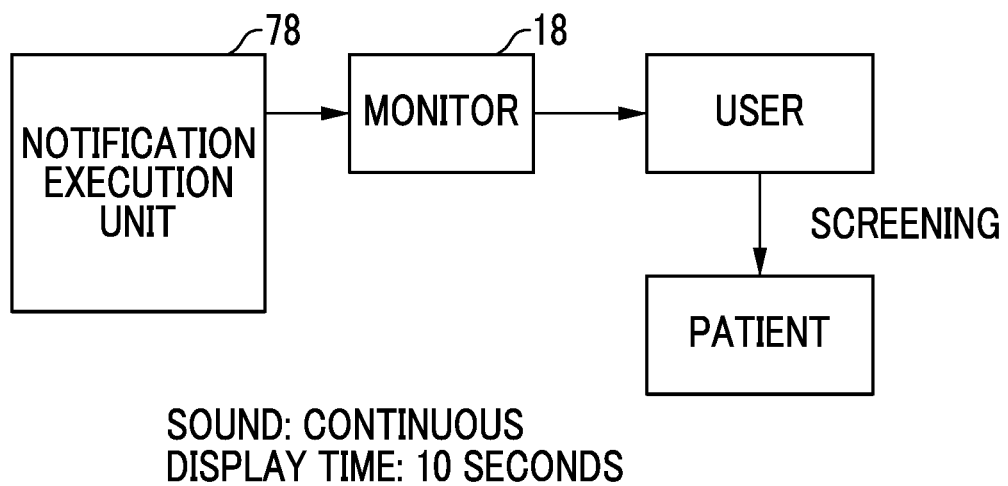
FIG. 18 is an explanatory diagram illustrating that the notification execution unit executes a notification according to notification setting information.

Next, in a case where the procedure information is selected and the notification setting information associated with the procedure name (refer to FIGS. 13 and 14), since the purpose of screening is to detect a region of interest, a sound output as the notification setting information is set as the continuous sound. Accordingly, as illustrated in FIG. 18, in a case where a region of interest is detected in the screening, a continuous sound is output from the speaker installed to the monitor 18, and a display indicating that a region of interest is performed on a part of the screen of the monitor 18 for "10 seconds". On the other hand, for example, in a case where the notification setting information associated with the ESD is set, since the treatment location is predetermined, notification setting information for not performing a notification even in a case where a region of interest is detected is set. Accordingly, even in a case where a region of interest is detected, a notification is not performed. In this case, in a case where another lesion is found, or in a case where it is necessary to perform inspection for a near location, the notification setting can be changed on the spot. The changed notification setting is automatically preserved as described below. As described above, in the notification setting information, a detailed notification method including not only how to perform a notification itself but also what to notify can be set. Moreover, it is possible to easily set the notification setting information. Accordingly, with the above-described configuration, it is possible to appropriately set a notification with respect to each user, and to prevent overlooking of a region of interest or the like.

The notification setting information setting unit 76 newly creates notification setting information associated with the individual setting information, and transmits the notification setting information to the notification setting information storage unit 74, and, as necessary, to the notification execution unit 78. In a case where individual setting information is not present, or in a case where notification setting information associated with the individual setting information is not changed, the notification setting information setting unit 76 newly creates notification setting information associated with the individual setting information. The case where individual setting information is not present is, for example, a case where a new user, a new patient, or the like is added to the four items of individual setting information used in this example. Specifically, the case where individual setting information is not present is a case of a user who uses the device first time, and in this case, notification setting information associated with individual setting information of the user is not present in the notification setting information storage unit 74. Further, a case where the currently set notification setting information is desired to be preserved after being changed is also included. For such a case, the notification setting information setting unit 76 preserves the notification setting information each time the notification setting information is created or changed. The preservation is automatic preservation which is usually performed without any instruction.

In the invention, a notification regarding the result of the image analysis processing is performed with respect to a user according to the notification setting information. In this example, in a case where a region of interest is detected by the region-of-interest detection unit 70 of the image analysis processing unit 61, a notification is performed according to the notification setting information. Accordingly, in the notification setting information, the setting of how to perform a notification in a case where a region of interest is detected is included. As the content of the notification setting, changes of a sound, vibration, a screen display aspect are exemplified. In case of a notification using a sound output, it is possible to set a place of the sound output, the type, pattern, and volume of the sound, and the like. In case of a notification using a vibration output, it is possible to set a place of the vibration output, the type, pattern, and degree of the vibration, and the like. In case of a notification using a screen output, it is possible to set a position where the notification screen is displayed, the size of the notification screen, an emphasizing method of the notification screen, a display time of the notification screen, and the like. These can be set to perform a notification with specific content by combining various notification settings like a ring tone of a mobile phone. The notification means is not limited to the changes of a sound, vibration, and a screen display aspect, and can be used as long as the notification means can be recognized by the user as described above.

Figure 19:
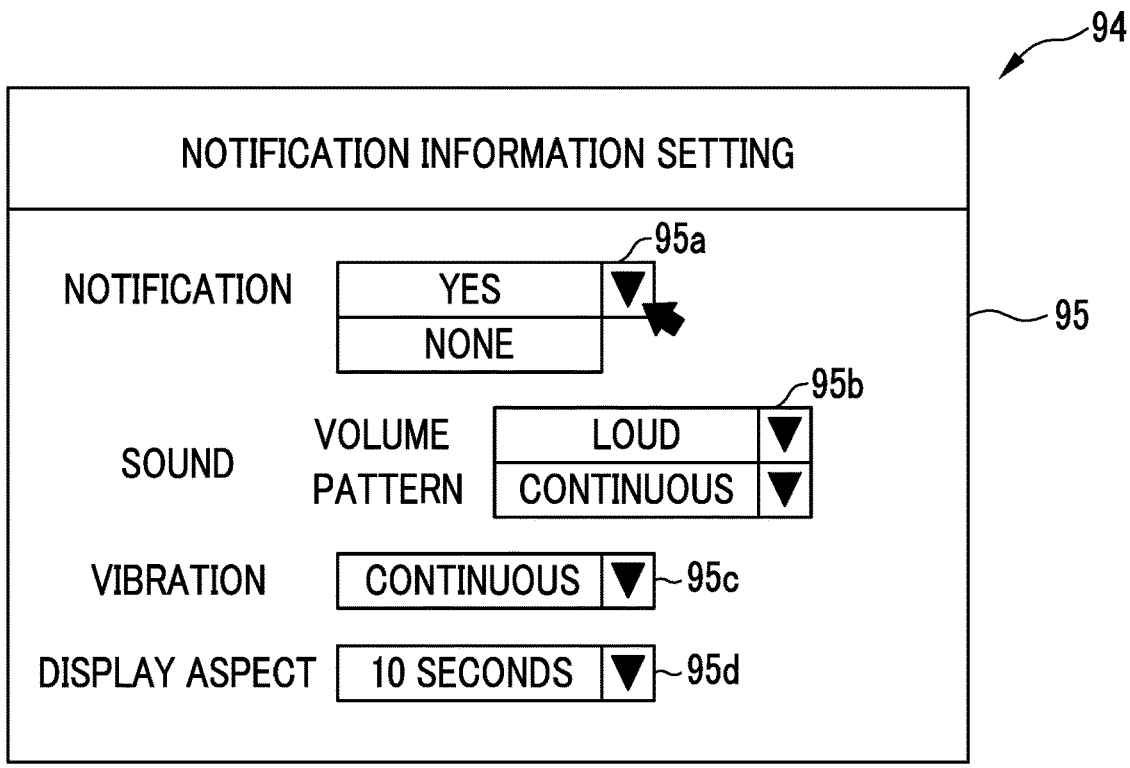
FIG. 19 is an image diagram illustrating a notification setting information setting screen (setting screen) in the monitor.
Figure 20:
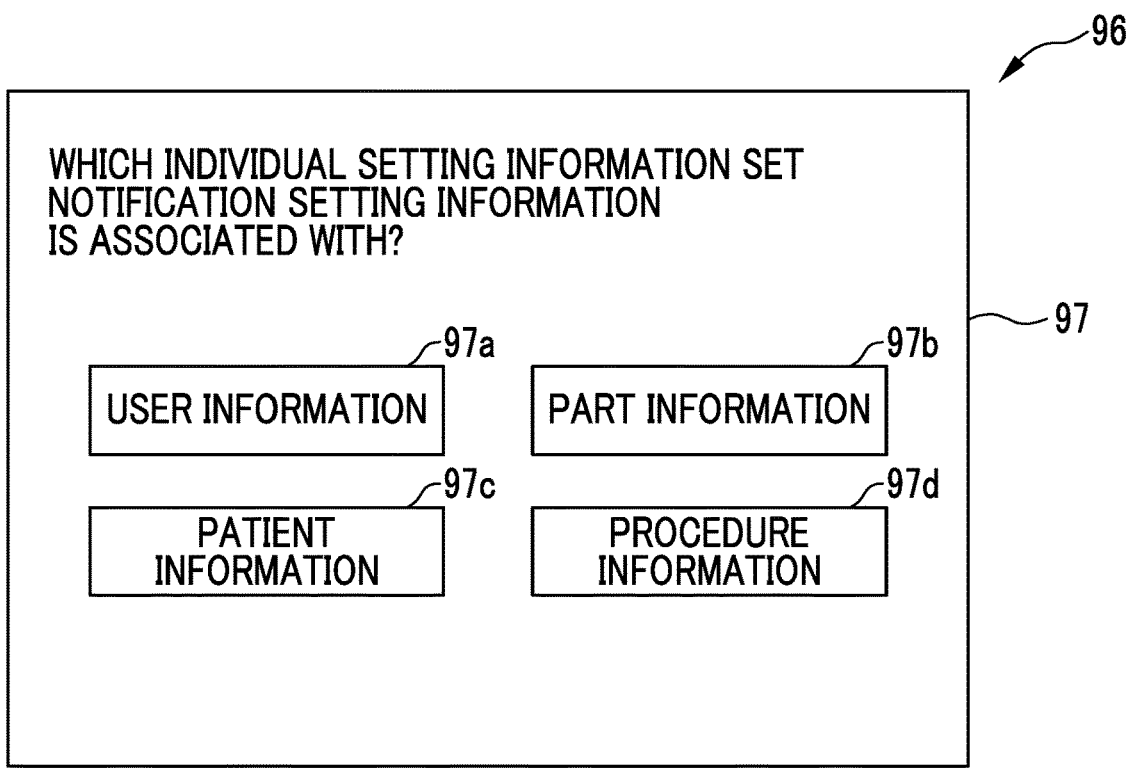
FIG. 20 is an image diagram illustrating an individual setting information setting screen (intermediate screen) in the monitor.

In this example, the notification setting information setting unit 76 creates notification setting information associated with individual setting information as follows. In the notification setting information setting screen (initial screen) 80 (refer to FIG. 5), a selection button 81*b* of "none" is selected for the individual setting information, it is regarded that the notification setting information associated with the individual setting information that the user desires to use is not present in the notification setting information storage unit 74, and as illustrated in FIG. 19, a notification setting information setting screen (setting screen) 94 including a notification setting information input region 95 is displayed to prompt the user to create notification setting information. In this example, the notification setting information input region 95 is configured to display options in a pop-up when an inverted triangle icon is clicked on the monitor 18. In the notification setting information input region 95, for the items of notification setting, notification setting information selection buttons 95*a* to 95*d* are selected to select desired contents. First, "yes" or "no" of a notification is selected. In case of selecting "no", the following input is not prompted. In case of selecting "yes" of a notification, for example, in a case where "loud" for the volume and "continuous sound" for the sound pattern as the item of a sound, "continuous" for the item of vibration, and "10 seconds" for the item of a display aspect are selected, at the time of executing a notification as in a case where a region of interest is detected, a notification in which a loud continuous sound is continuously output from a predetermined speaker, vibration means vibrates continuously, and a screen display is executed on a part of the monitor 18 for 10 seconds is executed. After an input in the notification setting information input region 95 is completed and the content of the notification setting is determined, as illustrated in FIG. 20, an individual setting information setting screen (intermediate screen) 96 including an individual setting information input region 97 is displayed, and individual setting information selection buttons 97*a* to 97*d* are selected to prompt the user to determine individual setting information to be associated with the notification setting information. For example, in a case where user information is selected as the individual setting information, an input of the user's ID or the like for identifying a user is prompted by the user information input screen 84 (refer to FIG. 7), and the creation of notification setting information associated with the individual setting information is completed.

By configuring the notification setting information setting unit 76 in this manner, the preservation of the notification setting information is automatically performed, and thus an optimal notification method can be set without a complicated operation by the user. In a case where there is notification setting information not associated with the individual setting information, the notification setting information setting unit 76 requests the user to associate the notification setting information with individual setting information. The case where there is notification setting information not associated with the individual setting information is, for example, a case where there is setting by the notification setting information and the setting is changed during the acquisition of a medical image or the like, and a case where it is unclear which individual setting information the notification setting information is to be associated with is exemplified.

The notification setting information storage unit 74 preserves the notification setting information associated with the individual setting information which is created by the notification setting information setting unit 76, each time the notification setting information setting unit 76 creates the notification setting information. Further, the notification setting information storage unit 74 is connected to the notification setting information selection unit 72, and the notification setting information selection unit 72 selects the notification setting information to be used (use-notification setting information) according to a user's instruction from the notification setting information preserved in the notification setting information storage unit 74. The case where the notification setting information is preserved in the notification setting information storage unit 74 each time the notification setting information setting unit 76 creates the notification setting information refers to a case in which when the notification setting information associated with the individual setting information is already present and any of the information (individual setting information and notification setting information) is changed, the changed information is automatically preserved in the notification setting information storage unit 74. In this case, it is possible to prevent the information before the change from being deleted unless there is an instruction from the user. The user can preserve and update the information before and after the change. Since the notification setting information storage unit 74 is configured in this manner, appropriate notification setting information is preserved without burden on the user. Accordingly, it is possible for the user to easily use the appropriately set notification setting in a specific case, and it is possible to prevent overlooking of a lesion or the like.

Figure 21:
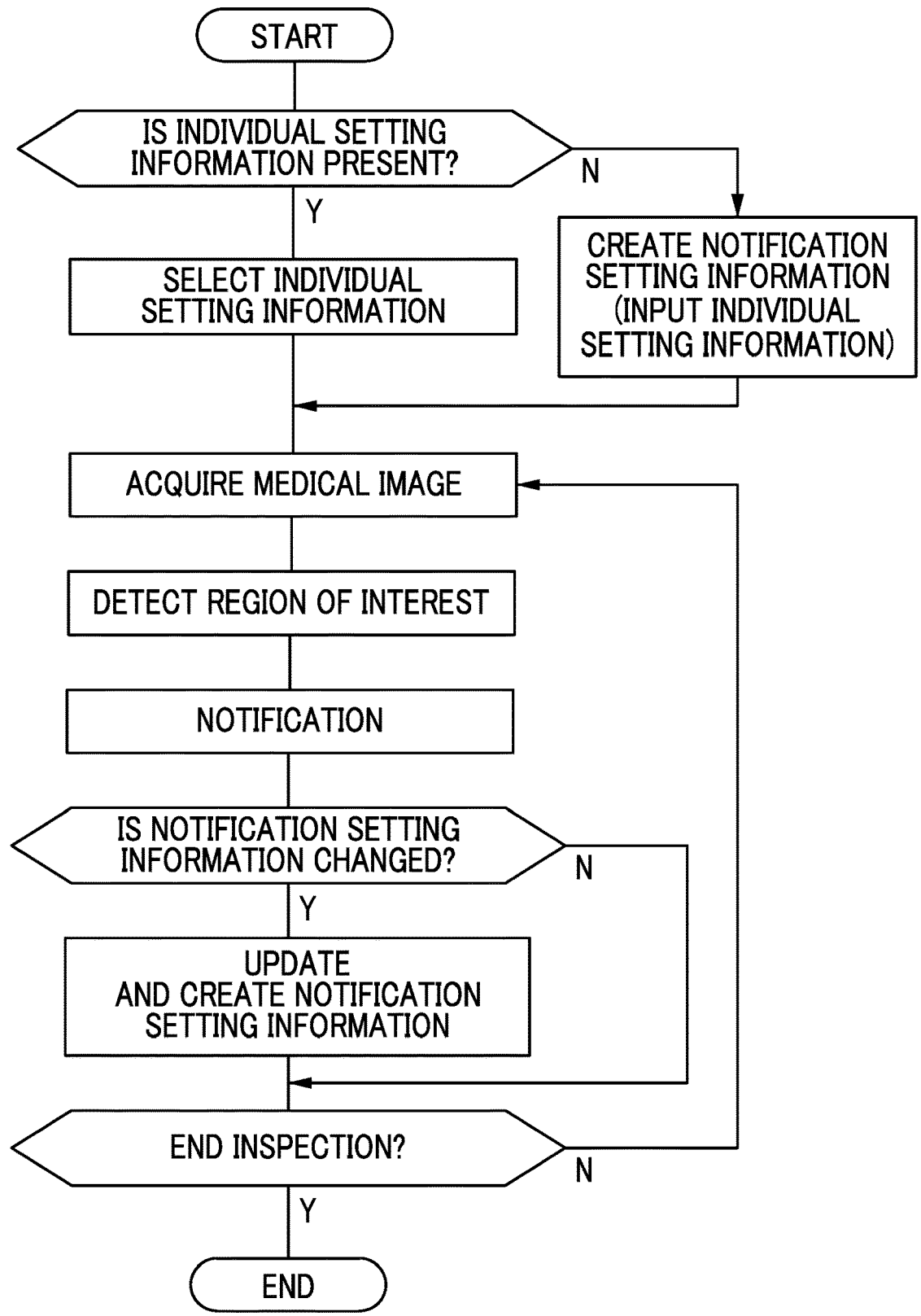
FIG. 21 is a flowchart illustrating a series of flows in the first embodiment.

Next, the embodiment is described along a series of flows. As illustrated in FIG. 21, the user selects, first, the notification setting information to be used, and performs an input regarding the individual setting information for creation or change (refer to FIG. 5). In a case where there is individual setting information associated with the notification setting information that the user desires to use, the individual setting information is input (refer to FIG. 6). According to the input content, the notification setting information selection unit 72 selects the notification setting information preserved in the notification setting information storage unit 74, and transmits the notification setting information as the use-notification setting information to the notification execution unit 78. Proceeding to the acquisition of a medical image, in a case where a region of interest is detected, a notification is performed according to the notification setting information. In a case where there is no individual setting information associated with the notification setting information that the user desires to use, after the creation of notification setting information (refer to FIGS. 19 and 20), similarly to the above case, proceeding to the acquisition of a medical image, in a case where a region of interest is detected during the acquisition of the medical image, a notification is performed according to the notification setting information.

In a case where the notification setting is modified so that notification setting information is changed during the acquisition of a medical image, it is possible to select overwriting the changed notification setting information on the notification setting information before change or newly preserving the changed notification setting information, but the notification setting information which is used at the end of inspection is preserved as the use-notification setting information. Accordingly, a notification can be performed by the same notification setting at the next inspection.

The above-described series of processing is repeatedly performed until inspection by the endoscope is ended.

Second Embodiment

Figure 22:
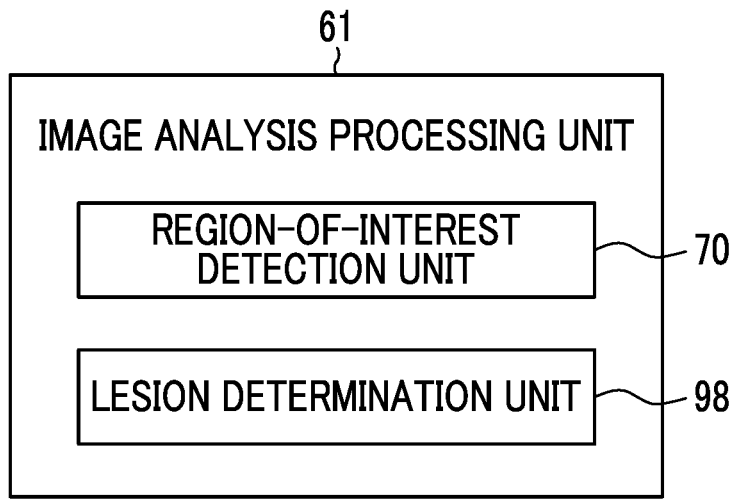
FIG. 22 is a block diagram illustrating an image analysis processing unit of a second embodiment.

In the embodiment, notification setting information is selected using lesion information such as the size of a lesion, as the individual setting information. As illustrated in FIG. 22, the image analysis processing unit 61 includes a lesion determination unit 98 in addition to the region-of-interest detection unit 70. The lesion determination unit 98 determines lesion information indicating the content of a lesion for the region of interest detected by the region-of-interest detection unit 70. Different notifications are performed depending on the contents of the lesion on the basis of the determination result. In FIGS. 22 to 30, the devices and the like with the same reference numerals as in FIGS. 1 to 21 are the same as those described in the first embodiment, and thus the description thereof is omitted. In this example, similarly to the region-of-interest detection unit 70, also in the lesion determination unit 98, lesion information indicating the content of the lesion is determined on the basis of, for example, a feature quantity obtained by color information and the gradient of the pixel values of the medical image, in addition to performing convolutional neural network on the medical image. In this example, as the lesion information, the lesion size, the lesion type, and a distance between a lesion and the distal end part 12d of the endoscope 12 (lesion distance) are used. The lesion size is the area of a portion determined as a lesion, and for example, three levels of "large", "medium", and "small" are included. The size of a lesion such as a polyp of 5 mm or more may be designated as a threshold value. The lesion type refers to the type of malignancy of a tumor, and includes, for example, a benign tumor (hyperplastic polyp (HP)), and a malignant tumor. Further, the distance to the lesion includes a distant view where the distance to the lesion is equal to or greater than a certain distance, and a near view where the distance to the lesion is less than a certain distance.

Figure 23:
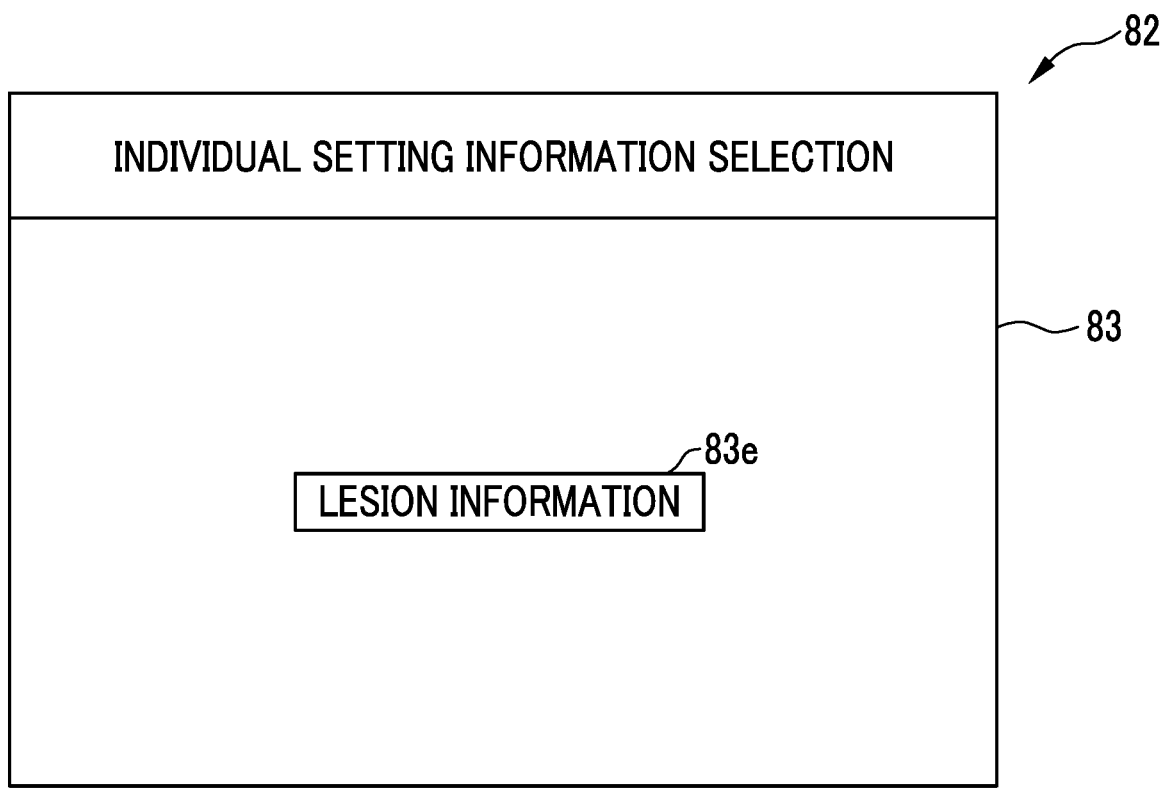
FIG. 23 is an image diagram illustrating an individual setting information selection screen in the monitor.

In this example, the lesion information is used as the individual setting information for selecting the notification setting information. In this case, similarly to the first embodiment, the user using the notification setting information read from the notification setting information storage unit 74 selects the selection button 81a of "present" of the selection region of the notification setting information setting screen (initial screen) 80 (refer to FIG. 5). Then, as illustrated in FIG. 23, individual setting information including "lesion information" 83e is displayed in the individual setting information selection screen 82.

Figures 24, 25:
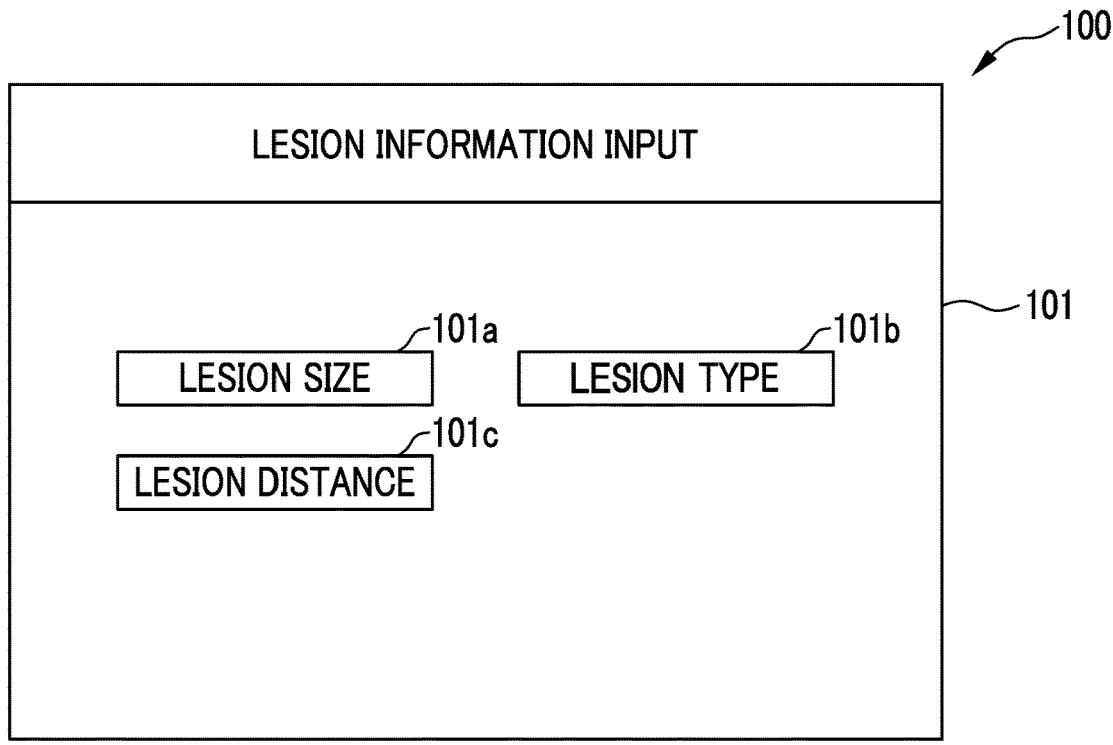
FIG. 24 is an image diagram illustrating a lesion information input screen in the monitor.
FIG. 25 is an image diagram illustrating a notification setting information display screen in the monitor.

In the individual setting information selection screen 82, in a case where the lesion information is selected as the individual setting information, as illustrated in FIG. 24, a lesion information input screen 100 including a lesion information input region 101 is displayed on the monitor 18. The lesion information input region 101 includes a region where any lesion information among a plurality of pieces of lesion information is selected by lesion information selection buttons 101a to 101c. The lesion information selection button is input using the user interface 19.

In a case where any lesion information among a plurality of pieces of lesion information is selected by the lesion information selection buttons 101*a* to 101*c*, as illustrated in FIG. 25, the details of the notification setting information of the selected lesion information is displayed in the notification setting information display screen 86 including the notification setting information detail display region 87. In this example illustrated in FIG. 25, the "lesion size" is selected as the lesion information, and the notification setting information of the "lesion size" is displayed in the notification setting information display screen 86.

As the notification setting information of the "lesion size", for example, in a case where the lesion size is "large", "notification: none" is displayed, which represents that a notification is not to be executed. Since the notification is not executed, the regions of "sound", "vibration", and "display aspect" are displayed with a symbol "-" meaning that there is no notification setting information relating thereto.

In a case where the lesion size is "medium", "notification: yes" is displayed, which represents that a notification is to be executed. Further, "sound: continuous" is displayed, which represents that a notification is to be executed by a sound output using a continuous sound. Further, "vibration: none" is displayed, which represents that a notification is not to be executed by a vibration output. Further, "display aspect: display time 10 seconds" is displayed, which represents that a notification is to be executed by a screen display output and the display time is 10 seconds.

In a case where the lesion size is "small", "notification: yes" is displayed, which represents that a notification is to be executed. Further, "sound: large" is displayed, which represents that a notification is to be executed by a sound output with a high level of volume. Further, "vibration: none" is displayed, which represents that a notification is not to be executed by a vibration output. Further, "display aspect: display time 30 seconds" is displayed, which represents that a notification is to be executed by a screen display output and the display time is 30 seconds.

Although not illustrated, in a case where "lesion type" is selected as the lesion information, the notification setting information of the "lesion type" is displayed in the notification setting information display screen 86. As the notification setting information of the "lesion type", for example, in a case where the lesion type is "benign tumor", "notification: none" is displayed, which represents that a notification is not to be executed. Since the notification is not executed, the regions of "sound", "vibration", and "display aspect" are displayed with a symbol "-" meaning that there is no notification setting information relating thereto. In a case where the lesion type is "malignant tumor", "notification: yes" is displayed, which represents that a notification is to be executed. Further, "sound: large" is displayed, which represents that a notification is to be executed by a sound output with a high level of volume. Further, "vibration: none" is displayed, which represents that a notification is not to be executed by a vibration output. Further, "display aspect: display time 30 seconds" is displayed, which represents that a notification is to be executed by a screen display output and the display time is 30 seconds.

Although not illustrated, in a case where "lesion distance" is selected as the lesion information, the notification setting information of the "lesion distance" is displayed in the notification setting information display screen 86. As the notification setting information of the "lesion distance", for example, in a case where the lesion distance is "distant view", "notification: yes" is displayed, which represents that a notification is to be executed. Further, "sound: large" is displayed, which represents that a notification is to be executed by a sound output with a high level of volume. Further, "vibration: none" is displayed, which represents that a notification is not to be executed by a vibration output. Further, "display aspect: display time 30 seconds" is displayed, which represents that a notification is to be executed by a screen display output and the display time is 30 seconds.

Figure 26:
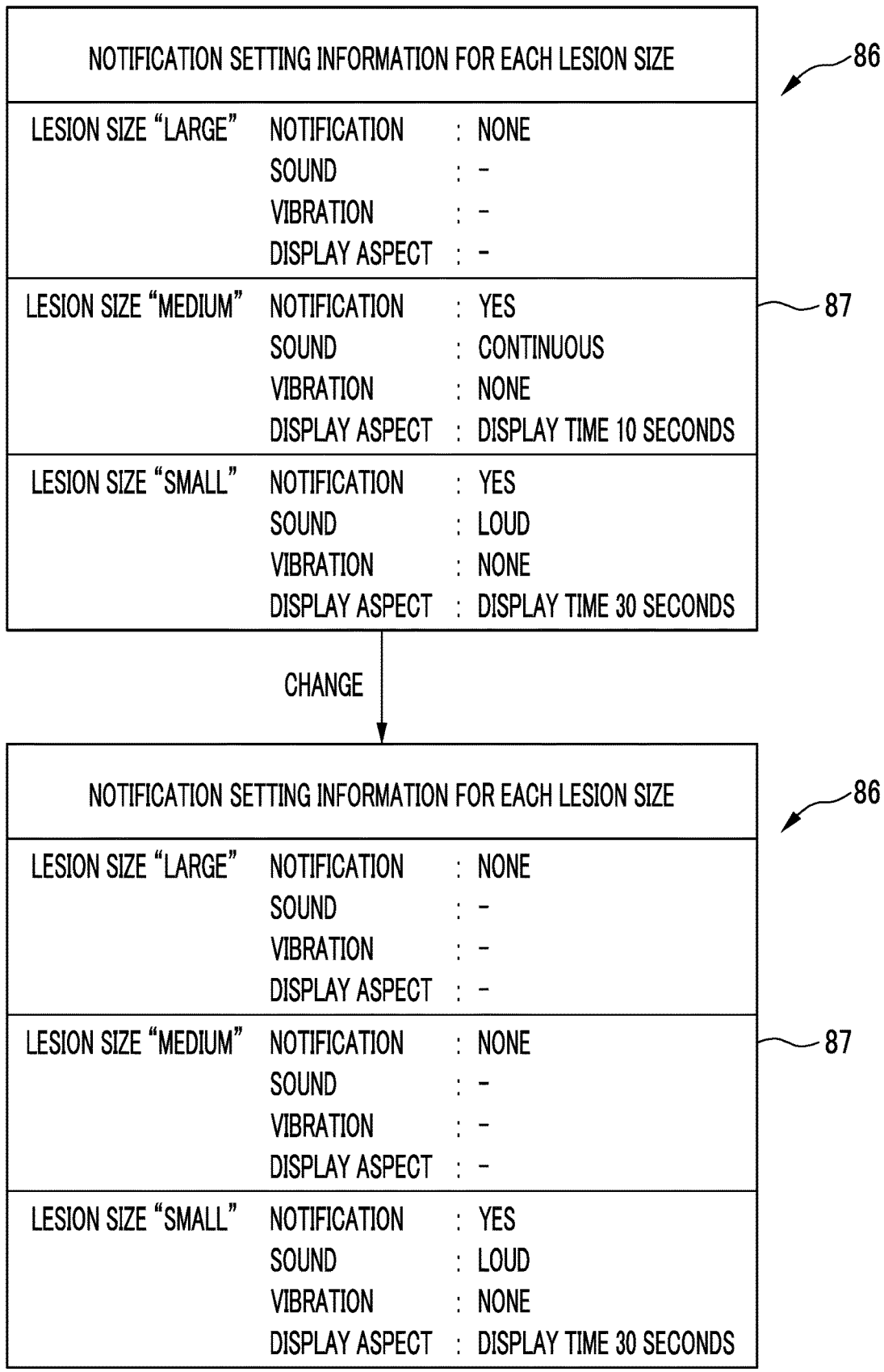
FIG. 26 is an explanatory diagram illustrating a notification setting information display screen in the monitor in a case where notification setting information is changed.

In a case where the lesion distance is "near view", "notification: yes" is displayed, which represents that a notification is to be executed. Further, "sound: continuous" is displayed, which represents that a notification is to be executed by a sound output using a continuous sound. Further, "vibration: none" is displayed, which represents that a notification is not to be executed by a vibration output. Further, "display aspect: display time 10 seconds" is displayed, which represents that a notification is to be executed by a screen display output and the display time is 10 seconds.

the content of the notification setting information of the lesion information can be appropriately changed. The upper diagram of FIG. 26 is the notification setting information display screen 86 according to the lesion information before change (refer to FIG. 25), and the lower diagram of FIG. 26 is the notification setting information display screen 86 according to the changed lesion information of which the content of the notification setting information of the lesion information is changed. The setting before change, in which a notification is not performed in a case where the lesion size is "large" and a notification is performed in a case where the lesion size is determined to be medium and small, is changed such that a notification is not performed in a case where the lesion size is large and medium and a notification is performed only in a case where the lesion size is determined to be small. The changed notification setting information created by the notification setting information setting unit 76 is preserved in the notification setting information storage unit 74, and by designating lesion information of any lesion size, it is easy to set again as the notification setting information associated with the lesion information.

Figure 27:
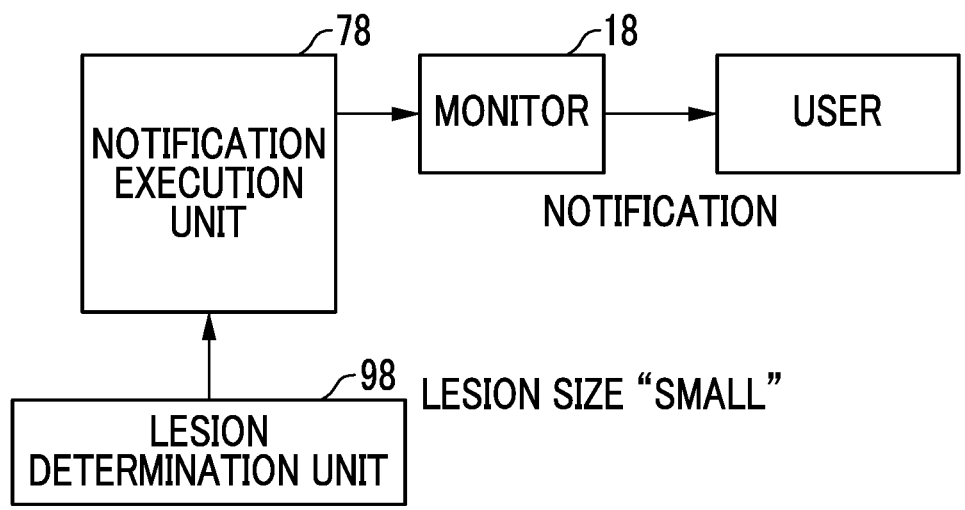
FIG. 27 is an explanatory diagram illustrating that the notification execution unit executes a notification according to notification setting information.

In this example, the notification by the notification execution unit 78 is executed as follows. In a case where "lesion size" is selected as the lesion information and the notification setting information associated with the lesion size is set (refer to FIG. 25), a notification is performed according to the notification setting information. That is, as illustrated in FIG. 27, in a case where it is determined that a lesion having a size of "small" is present in the acquired image, a notification is performed, a sound is output from the speaker installed to the monitor 18, and an image is output to the screen of the monitor 18.

Figure 28:
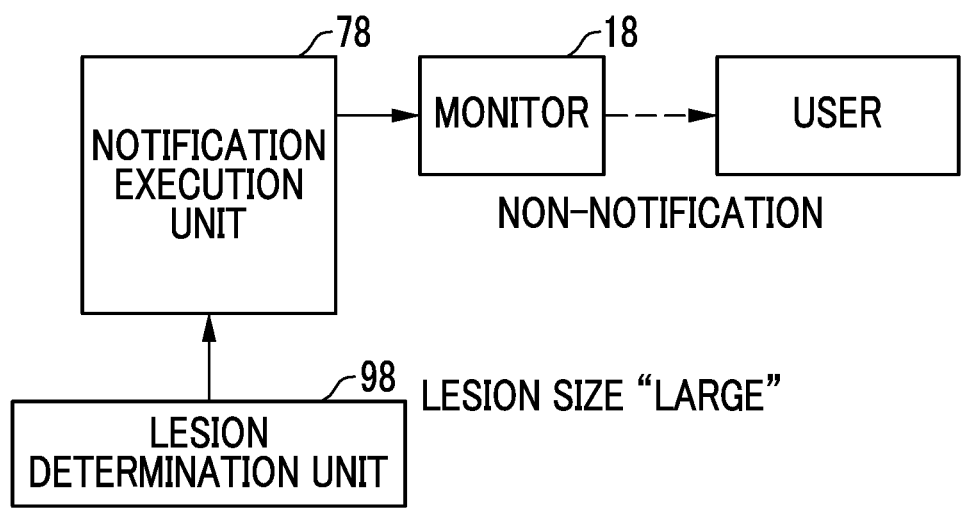
FIG. 28 is an explanatory diagram illustrating that the notification execution unit executes a notification according to notification setting information.

As illustrated in FIG. 28, in a case where it is determined that a lesion having a size of "large" is present in the acquired image, a notification is not performed. Accordingly, a sound is not output from the speaker installed to the monitor 18, and an image is not output to the screen of the monitor 18.

In a case where a notification is not performed, in some cases, it may not be known whether the non-notification is non-notification because the region of interest is not detected by the region-of-interest detection unit 70 (non-notification due to non-detection), or non-notification depending on the setting in the notification setting information in which a notification is not performed (non-notification due to setting). For this, it is possible to confirm whether the non-notification is either non-notification due to non-detection or non-notification due to setting. The confirmation can be performed by a confirmation button 13*c* provided to the operation part 12*b* of the endoscope, for example.

Figure 29:
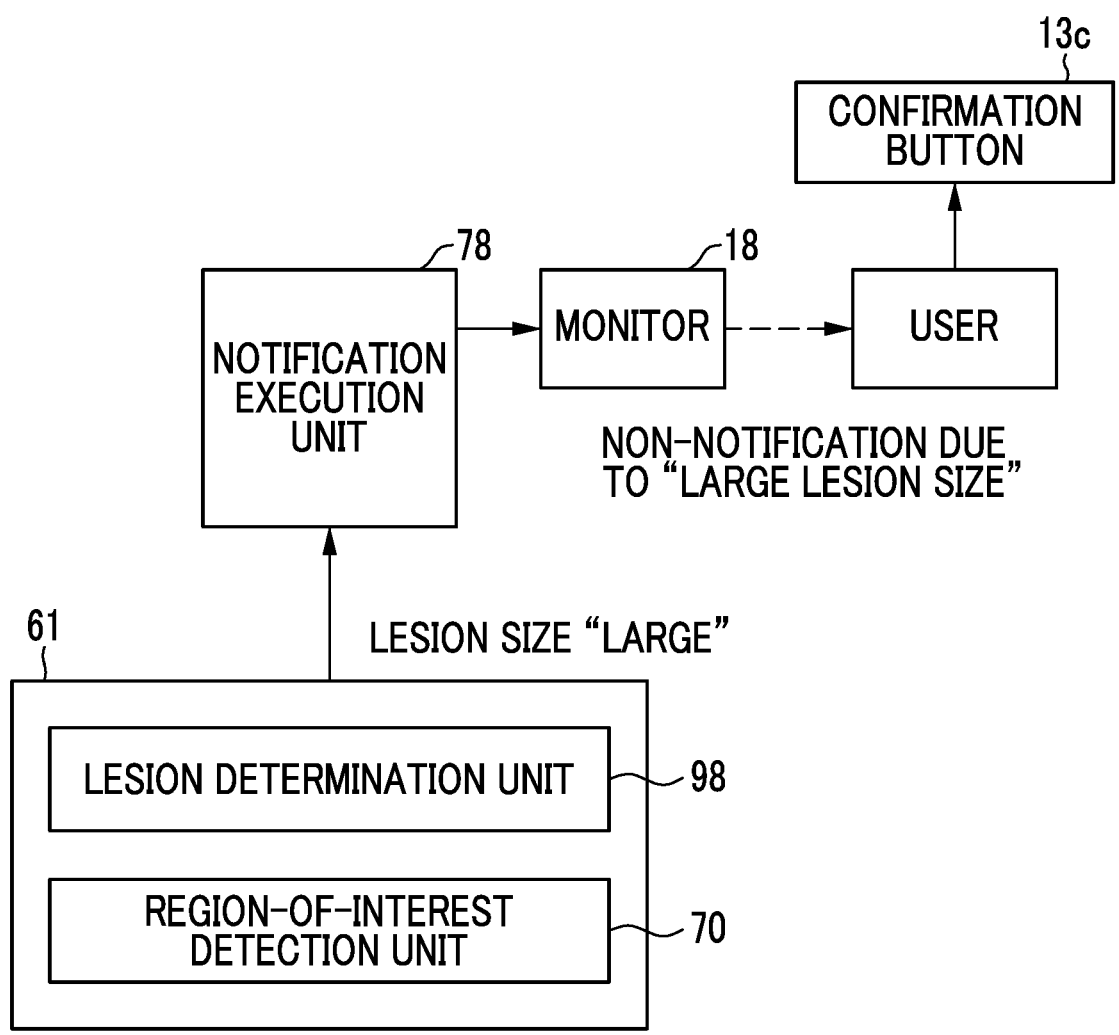
FIG. 29 is an explanatory diagram illustrating that confirmation of notification setting information is performed.

For example, as illustrated in FIG. 29, in a case where the lesion size in the notification setting information is "large", a notification is not performed. In this case, in a case where the user operates the confirmation button 13c, as illustrated in FIG. 29, a message "non-notification due to 'large' lesion size" is displayed on the monitor 18. In this manner, it is possible for the user to recognize that the non-notification is due to notification setting information.

Figure 30:
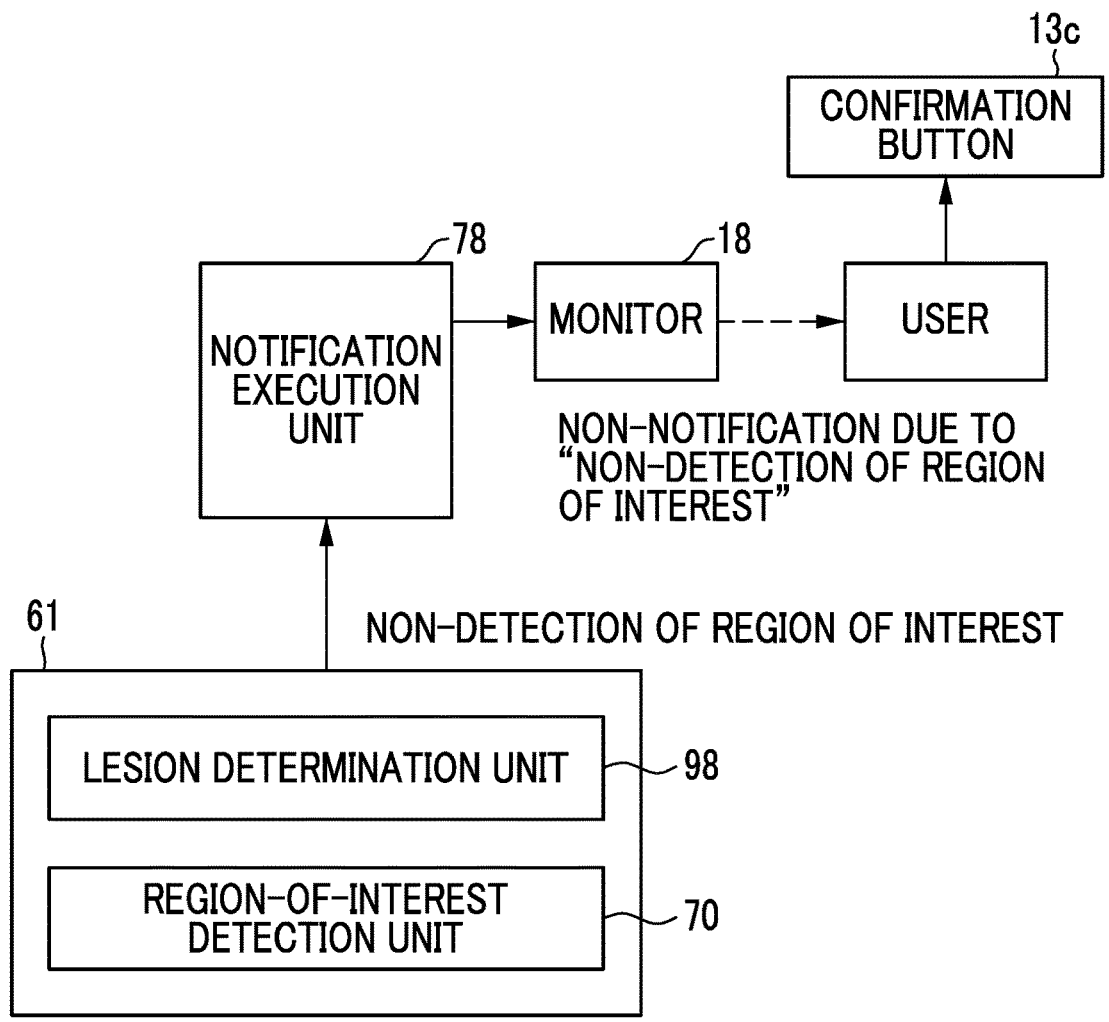
FIG. 30 is an explanatory diagram illustrating that confirmation of notification setting information is performed.

On the other hand, although the user founds a region having a possibility of a lesion, a region of interest is not detected by the region-of-interest detection unit 70, and a notification due to the detection of a region of interest is not performed in some cases. In this case, as illustrated in FIG. 30, in a case where the user operates the confirmation button 13c, a message "non-notification due to 'non-detection of region of interest'" is displayed on the monitor 18. In this manner, it is possible for the user to recognize that the non-notification is due to non-detection of a region of interest.

As described above, in this example, a configuration including the lesion determination unit 98 and the notification control unit 67 is adopted, the user can arbitrarily set the level of a notification, and the setting can be tailored to the technique or the level of proficiency of the user. Accordingly, the device can be easy to perform diagnosis, from the beginner for which a notification is preferably performed even in a case where the lesion is relatively easy to detect, to the expert for which an excessive notification is preferably reduced. Further, it is also possible to use a notification as a guide for the user to evaluate his/her level objectively.

In the embodiment, the invention is applied to the endoscope system that performs processing on the endoscopic image as one of the medical images. However, the invention can also be applied to a medical image processing device that processes medical images other than the endoscopic image. The invention can also be applied to a diagnosis support apparatus for performing diagnosis support for a user using the medical image. The invention can also be applied to a medical service support apparatus for supporting the medical service, such as a diagnostic report, using the medical image.

It is preferable that the medical image is a normal light image that is obtained from the application of light in a white-light wavelength range or light in a plurality of wavelength ranges as the light in a white-light wavelength range.

It is preferable that the medical image is a special light image that is obtained from the application of light in a specific wavelength range, and the specific wavelength range is a range narrower than the white-light wavelength range. It is preferable that the specific wavelength range is included in a blue-light wavelength range or a green-light wavelength range of a visible-light wavelength range. It is preferable that the specific wavelength range includes a wavelength range of 390 nm to 450 nm or 530 nm to 550 nm, and light in the specific wavelength range has a peak wavelength in a wavelength range of 390 nm to 450 nm or 530 nm to 550 nm.

It is preferable that the specific wavelength range is included in a red-light wavelength range of a visible-light wavelength range. It is preferable that the specific wavelength range includes a wavelength range of 585 nm to 615 nm or 610 nm to 730 nm, and light in the specific wavelength range has a peak wavelength in a wavelength range of 585 nm to 615 nm or 610 nm to 730 nm.

It is preferable that the specific wavelength range includes a wavelength range where a light absorption coefficient in oxyhemoglobin is different from that in reduced hemoglobin, and light in the specific wavelength range has a peak wavelength in a wavelength range where a light absorption coefficient in oxyhemoglobin is different from that in reduced hemoglobin. It is preferable that the specific wavelength range includes a wavelength range of 400±10 nm, 440±10 nm, 470±10 nm, or 600 nm to 750 nm, and light in the specific wavelength range has a peak wavelength in a wavelength range of 400±10 nm, 440±10 nm, 470±10 nm, or 600 nm to 750 nm.

It is preferable that the medical image is an in-vivo image of the inside of a living body, and the in-vivo image has information of fluorescence emitted by fluorescent materials in the living body. It is preferable that the fluorescence is obtained from the application of excitation light of which a peak wavelength is included in a wavelength range of 390 nm to 470 nm, to the inside of the living body.

It is preferable that the medical image is an in-vivo image of the inside of a living body, and the specific wavelength range is an infrared wavelength range. It is preferable that the specific wavelength range includes a wavelength range of 790 nm to 820 nm or 905 nm to 970 nm, and light in the specific wavelength range has a peak wavelength in a wavelength range of 790 nm to 820 nm or 905 nm to 970 nm.

It is preferable that an image acquisition unit includes a special light image acquisition unit that acquires a special light image having a signal in the specific wavelength range on the basis of a normal light image obtained from the application of light in a white-light wavelength range or light in a plurality of wavelength ranges as the light in a white-light wavelength range, and the medical image is the special light image.

It is preferable that the signal in the specific wavelength range is obtained from an arithmetic operation based on color information about RGB or CMY included in the normal light image.

It is preferable that a computed image generation unit generating a computed image from an arithmetic operation based on at least one of the normal light image that is obtained from the application of light in a white-light wavelength range or light in a plurality of wavelength ranges as the light in a white-light wavelength range or the special light image that is obtained from the application of light in a specific wavelength range is provided, and the medical image is the computed image.

In the embodiment, the hardware structure of the processing units executing various kinds of processing, such as the region-of-interest detection unit 70 and the lesion determination unit 98 included in the image analysis processing unit 61, and the notification setting information selection unit 72, the notification setting information storage unit 74, the notification setting information setting unit 76, and the notification execution unit 78 included in the notification control unit 67 is various processors as follows. The various processors include a central processing unit (CPU) as a general-purpose processor functioning as various processing units by executing software (program), a programmable logic device (PLD) as a processor of which the circuit configuration can be changed after manufacturing such as a field programmable gate array (FPGA), and a dedicated electrical circuit (graphical processing unit (GPU)) as a processor having a circuit configuration designed exclusively for executing various kinds of processing.

One processing unit may be configured by one of the various processors, or configured by a combination of the same or different kinds of two or more processors (for example, combination of a plurality of FPGAs, combination of the CPU and the FPGA, combination of the CPU and the GPU). In addition, a plurality of processing units may be configured by one processor. As an example where a plurality of processing units are configured by one processor, first, there is an aspect where one processor is configured by a combination of one or more CPUs and software as typified by a computer, such as a client or a server, and this processor functions as a plurality of processing units. Second, there is an aspect where a processor fulfilling the functions of the entire system including a plurality of processing units by one integrated circuit (IC) chip as typified by a system on chip (SoC) or the like is used. Thus, various processing units are configured by using one or more of the above-described various processors as hardware structures.

Furthermore, the hardware structures of the various processors are more specifically electrical circuitry in a form in which circuit elements, such as semiconductor elements, are combined.

Figure 31:
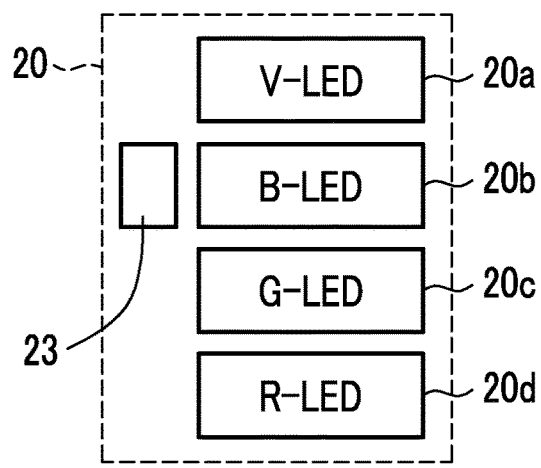
FIG. 31 is a block diagram illustrating a light source unit comprising a plurality of LEDs.

In the embodiment, it is preferable that illumination light is emitted by using LEDs of four colors, such as a violet light emitting diode (V-LED) 20a, a blue light emitting diode (B-LED) 20b, a green light emitting diode (G-LED) 20c, and a red light emitting diode (R-LED) 20d, and a wavelength cut filter 23 as the light source unit 20, as illustrated in FIG. 31.

The V-LED 20a emits violet light V in a wavelength range of 380 nm to 420 nm. The B-LED 20b emits blue light B in a wavelength range of 420 nm to 500 nm. Among the blue light B emitted from the B-LED 20b, at least light in a wavelength range on the longer wavelength side than a peak wavelength of 450 nm is cut by the wavelength cut filter 23. In this manner, blue light Bx transmitted through the wavelength cut filter 23 is within a wavelength range of 420 nm to 460 nm. The reason of cutting light in a wavelength range on the longer wavelength side than 460 nm is that light in a wavelength range on the longer wavelength side than 460 nm is a factor reducing a blood vessel contrast of the blood vessel as the observation target. The wavelength cut filter 23 may attenuate light in a wavelength range on the longer wavelength side than 460 nm instead of cutting light in a wavelength range on the longer wavelength side than 460 nm. The G-LED 20c emits green light G having a wavelength range of 480 nm to 600 nm. The R-LED 20d emits red light R having a wavelength range of 600 nm to 650 nm.

Figure 32:
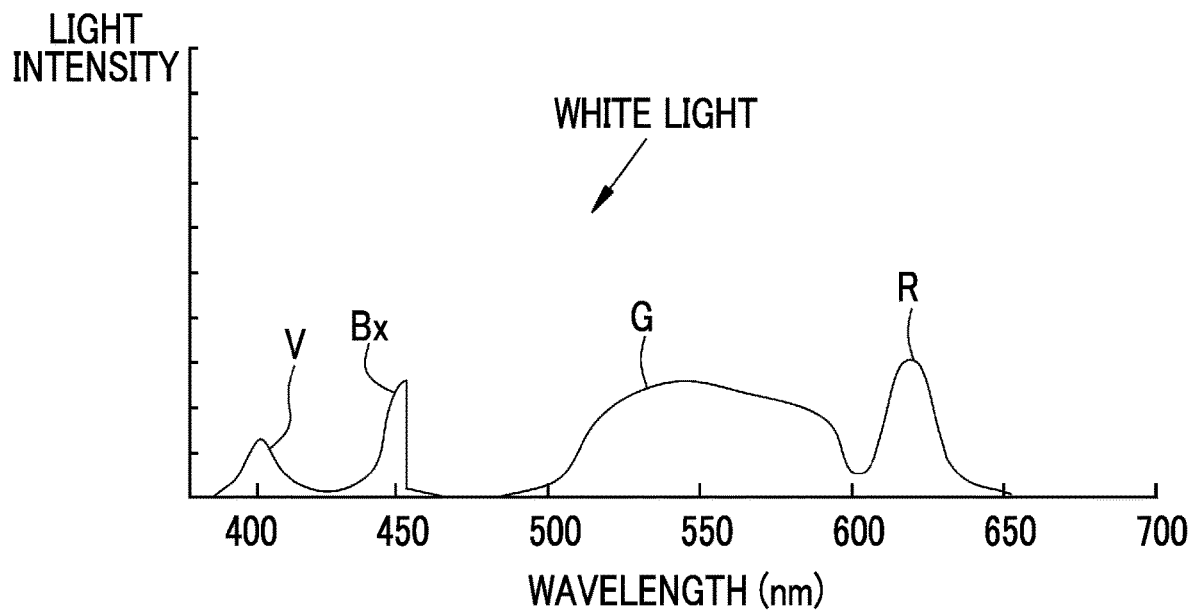
FIG. 32 is a graph illustrating a spectrum of white light obtained by emission of a plurality of LEDs.
Figure 33:
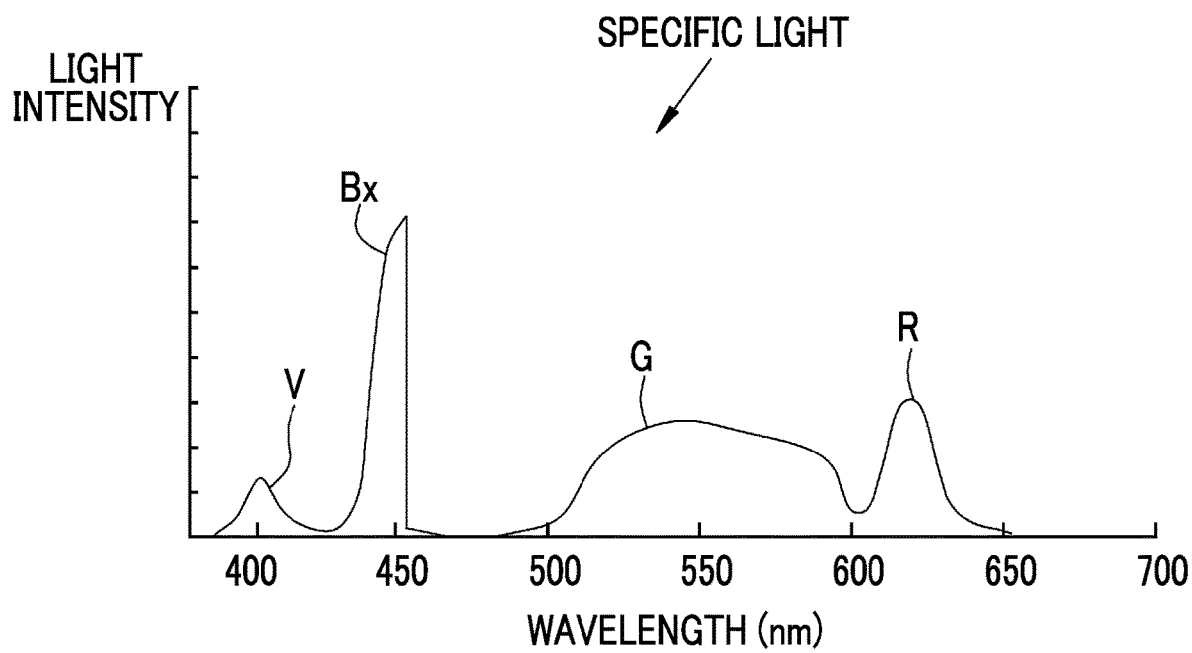
FIG. 33 is a graph illustrating a spectrum of specific light obtained by emission of a plurality of LEDs.

In a case where light in a white-light wavelength range (white light) is emitted, all of the V-LED 20a, the B-LED 20b, the G-LED 20c, and the R-LED 20d are turned on. In this manner, as illustrated in FIG. 32, the light source device 14 emits white light including violet light V, blue light Bx, green light and red light R. Since white light has an intensity of a certain level or greater from the blue-light wavelength rang to the red-light wavelength range, white light is almost white. In a case where specific light having a peak wavelength in a wavelength range of 440±10 nm is emitted as the light in a specific wavelength range (specific light), for example, as illustrated in FIG. 33, specific light in which the light emission amount of blue light Bx is greater than any light emission amount of violet light V, green light and red light R is emitted.

Figure 34:
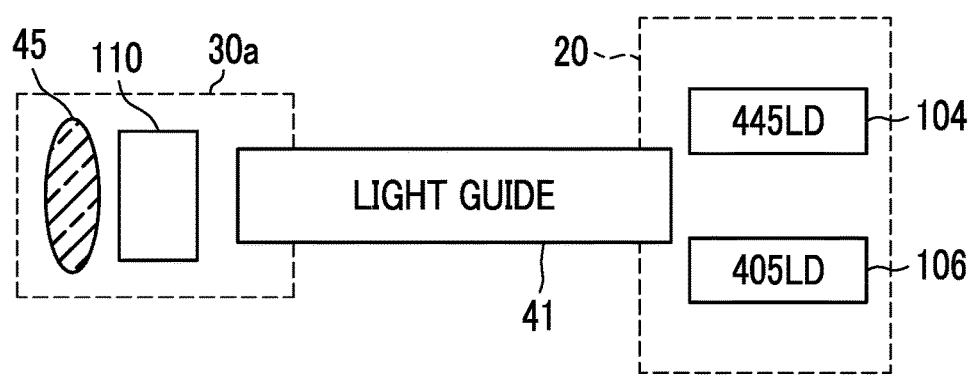
FIG. 34 is a block diagram illustrating a light source unit comprising a laser light source, and a phosphor.

In the embodiment, illumination light may be emitted using the laser light source and a phosphor. In this case, as illustrated in FIG. 34, the light source unit 20 is provided with a blue laser light source (indicated as "445LD", LD indicates a "laser diode") 104 that emits blue laser light having a peak wavelength of 445±10 nm, and a blue-violet laser light source (indicated as "405LD") 106 that emits blue-violet laser light having a peak wavelength of 405±10 nm.

The illumination optical system 30a is provided with a phosphor 110 on which blue laser light or blue-violet laser light is incident from the light guide 41, in addition to the illumination lens 45. The phosphor 110 is excited by blue laser light to emit fluorescence. In addition, some of blue laser light is transmitted without exciting the phosphor 110. Blue-violet laser light is transmitted without exciting the phosphor 110. Light from the phosphor 110 illuminates the body of the observation target via the illumination lens 45.

Figure 35:
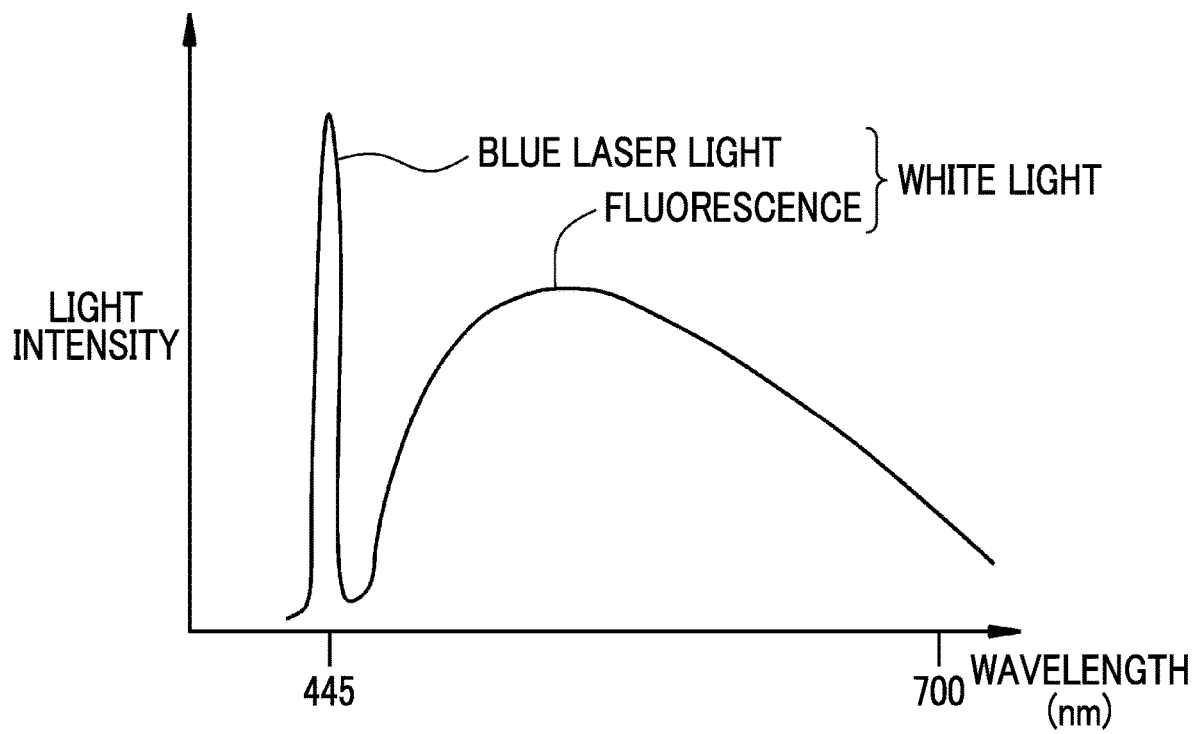
FIG. 35 is a graph illustrating a spectrum of white light emitted using a laser light source and a phosphor.
Figure 36:
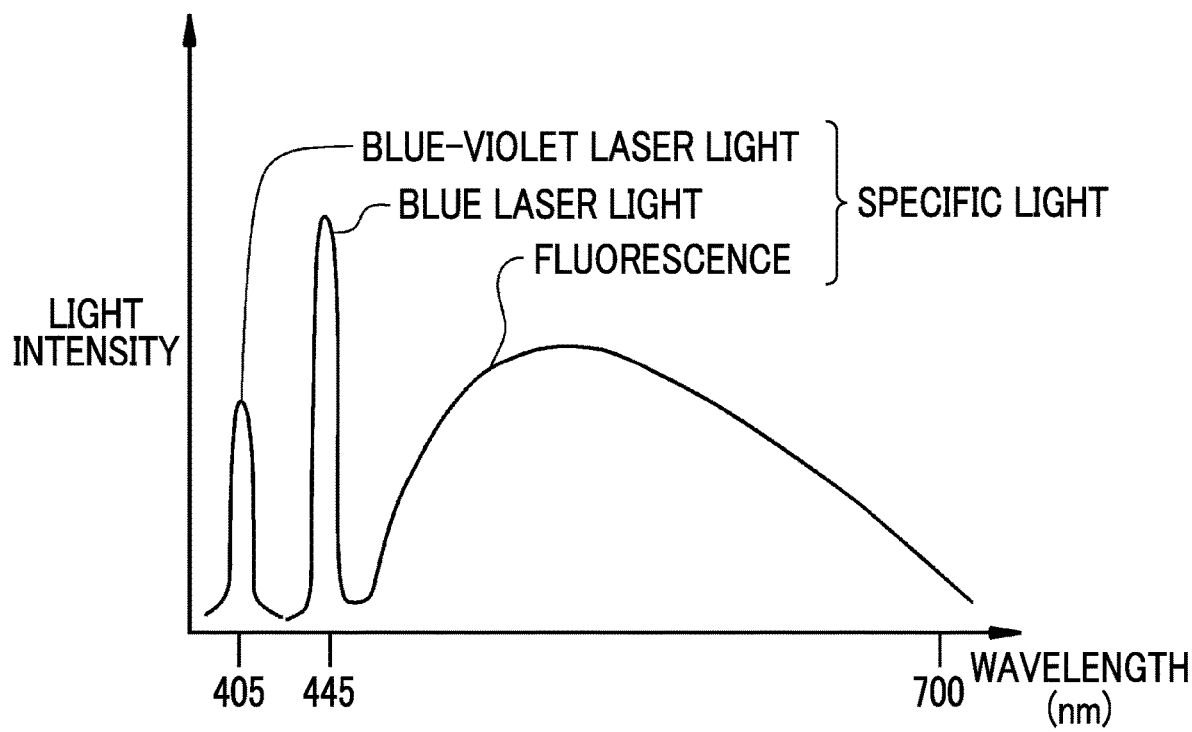
FIG. 36 is a graph illustrating a spectrum of specific light emitted using a laser light source and a phosphor.

Here, in a case where white light is emitted, the blue laser light source 104 is turned on so that blue laser light is mainly incident on the phosphor 110, and thus white light in which blue laser light and fluorescence emitted from the phosphor 110 excited by blue laser light are combined, as illustrated in FIG. 35 is emitted. Meanwhile, in a case where specific light having a peak wavelength in a wavelength range of 440±10 nm is emitted as the light in a specific wavelength range (specific light), the blue laser light source 104 and the blue-violet laser light source 106 are turned on so that both blue-violet laser light and blue laser light are incident on the phosphor 110. In this manner, specific light in which blue-violet laser light, blue laser light, and fluorescence emitted from the phosphor 110 excited by blue laser light are combined, as illustrated in FIG. 36 is emitted.

It is preferable that the half-width of blue laser light or blue-violet laser light is about ±10 nm. As the blue laser light source 104 and the blue-violet laser light source 106, broad area type InGaN laser diodes can be used, and InGaNAs laser diodes and GaNAs laser diodes can also be used. A configuration using a light emitter such as a light emitting diode may be used as the light source.

It is preferable to use the phosphor 110 configured to include a plurality of types of phosphors that absorb some of blue laser light to emit light from green to yellow by excitation (for example, YAG phosphor or phosphor such as BAM ($BaMgAl_{10}O_{17}$)). In a case where a semiconductor light emitting element is used as an excitation light source of the phosphor 110 as in this configuration example, it is possible to obtain high intensity white light with high luminous efficiency, to easily adjust the intensity of white light, and suppress changes in color temperature and chromaticity of white light to be small.

Figure 37:
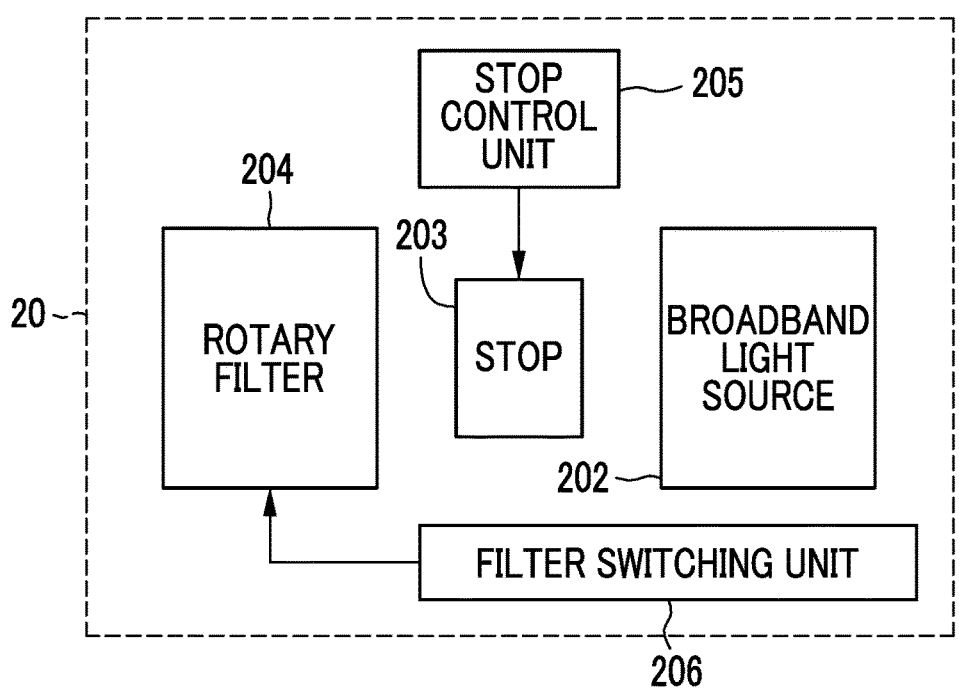
FIG. 37 is a block diagram illustrating a light source unit comprising a broadband light source and a rotary filter.

In the embodiment, illumination light may be emitted using a broadband light source such as a xenon lamp and a rotary filter. In this case, as illustrated in FIG. 37, a broadband light source 202, a rotary filter 204, and a filter switching unit 206 are provided in the light source unit 20. Further, a stop 203 is provided between the broadband light source 202 and the rotary filter 204, and the area of the opening of the stop 203 is adjusted by a stop control unit 205. The stop control unit 205 controls the stop 203 on the basis of dimming signals from the processor device 16.

The broadband light source 202 is a xenon lamp, a white LED, or the like, and emits broadband light having a wavelength range from blue to red. The rotary filter 204 comprises a white light filter 210 provided on the inner side closest to the rotation axis, and a specific light filter 212 provided on the outer side of the white light filter 210 (refer to FIG. 38).

The filter switching unit 206 moves the rotary filter 204 in a radial direction. Specifically, the filter switching unit 206 inserts the white light filter 210 to the light path of broadband light in a case where white light is emitted. The filter switching unit 206 inserts the specific light filter 212 to the light path of broadband light in a case where light in a specific wavelength range (specific light) is emitted.

Figure 38:
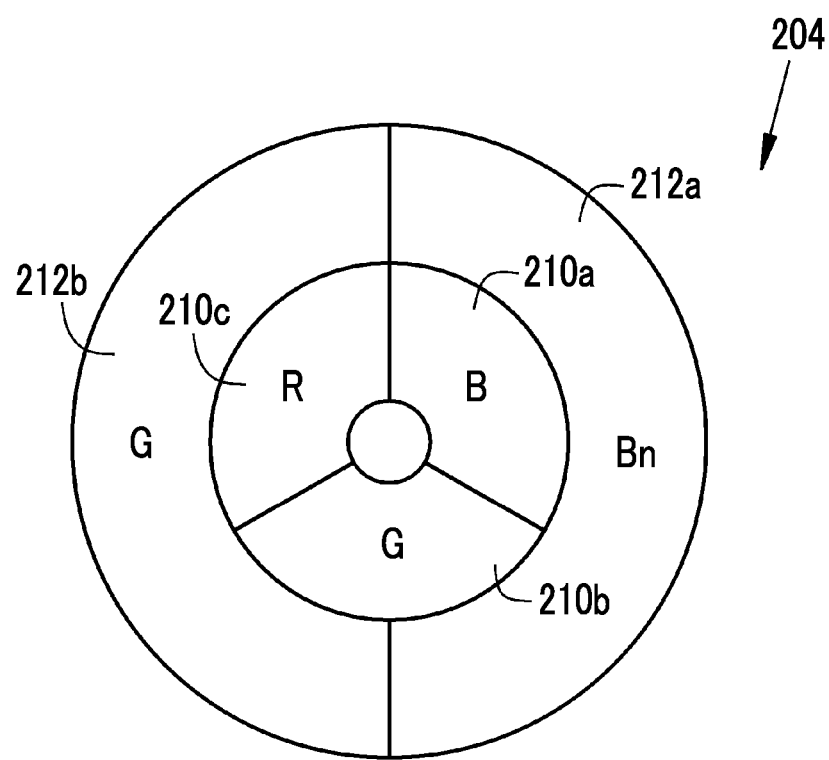
FIG. 38 is a plan view illustrating a rotary filter.

As illustrated in FIG. 38, the white light filter 210 is provided with a B filter 210a, a G filter 210b, and an R filter 210c along the circumferential direction. The B filter 210a transmits broadband blue light B having a wavelength range of 400 nm to 500 nm among broadband light. The G filter 210b transmits green light G among broadband light. The R filter 210c transmits red light R among broadband light. Accordingly, in a case where white light is emitted, as white light, blue light B, green light and red light R are sequentially emitted by the rotation of the rotary filter 204.

The specific light filter 212 is provided with a Bn filter 212a, and a G filter 212b along the circumferential direction. The Bn filter 212a transmits blue narrow-band light Bn having a wavelength range of 400 nm to 450 nm among broadband light. The G filter 212b transmits green light G among broadband light. Accordingly, in a case where specific light is emitted, as specific light, blue narrow-band light Bn and green light G are sequentially emitted toward the observation target by the rotation of the rotary filter 204.

In a case where illumination light is emitted using the broadband light source such as a xenon lamp and the rotary filter, at the time of illumination of white light, the observation target is imaged using a monochrome image sensor each time the observation target is illuminated with blue B, green light and red light R. An image comprising white light components is generated by the B image, the G image, and the R image obtained by imaging the observation target. Further, at the time of illumination of specific light, the observation target is imaged using a monochrome image sensor each time the observation target is illuminated with the blue narrow-band light Bn and green light and an image comprising specific light components is generated by the Bn image and the G image obtained by such imaging.

EXPLANATION OF REFERENCES

10: endoscope system (medical image processing device)
12: endoscope
12a: insertion part
12b: operation part
12c: bendable part
12d: distal end part
12e: angle knob
12f: forceps inlet
13a: zoom operation part
13b: scope switch
13c: confirmation button
14: light source device
16: processor device
18: monitor
19: user interface
KB: keyboard
MS: mouse
FS: foot switch
SB: switching switch
DB: confirm switch
20: light source unit
20a: V-LED
20b: B-LED
20c: G-LED
20d: R-LED
22: light source control unit
41: light guide
30a: illumination optical system
30b: imaging optical system
45: illumination lens
46: objective lens
47: zoom lens
48: image sensor
52: control unit
54: image acquisition unit
56: DSP
58: noise reduction unit
59: conversion unit
61: image analysis processing unit
66: display control unit
67: notification control unit
68: medical service support apparatus
70: region-of-interest detection unit
72: notification setting information selection unit
74: notification setting information storage unit
76: notification setting information setting unit
78: notification execution unit
79: information storage unit
80: notification setting information setting screen (initial screen)
81: selection region
81a, 81b: selection button
82: individual setting information selection screen
83: individual setting information selection region
83a, 83b, 83c, 83d: individual setting information selection button
84: user information input screen
85: user information input region
86: notification setting information display screen
87: notification setting information detail display region
88: patient information input screen
89: patient information input region
90: part information input screen
91: part information input region
91a, 91b, 91c, 91d: part information selection button
92: procedure information input screen
93: procedure information input region
93a, 93b, 93c: procedure information selection button
94: notification setting information setting screen (setting screen)
95: notification setting information input region
95a, 95b 95c, 95d: notification setting information selection button
96: individual setting information setting screen (intermediate screen)
97: individual setting information input region
97a, 97b, 97c, 97d: individual setting information selection button
98: lesion determination unit
100: lesion information input screen
101: lesion information input region
104: blue laser light source
106: blue-violet laser light source
110: phosphor
202: broadband light source
203: stop
204: rotary filter
205: stop control unit
206: filter switching unit
210a: B filter
210b: G filter
210c: R filter
212a: Bn filter
212b: G filter

What is claimed is:

1. A medical image processing device comprising: a processor configured to function as:
- an image acquisition unit that acquires a medical image including a subject;
- an image analysis processing unit that performs image analysis processing on the medical image;
- a notification execution unit that performs a notification to notify a user of a result of the image analysis processing according to notification setting information, wherein notification setting refers to setting of a notification content regarding which method the notification is performed and the notification setting information refers to data for setting the notification setting;
- a notification setting information storage unit that preserves the notification setting information in association with individual selling information different from the notification setting information, wherein the individual setting information includes a plurality of item information; and
- a notification setting information selection unit that selects use-notification setting information by using the one of the plurality of item information of the individual setting information, from the notification setting information preserved in the notification setting information storage unit,
- wherein the notification execution unit performs a notification with different methods of the notifications for different lesion sizes determined based on the result of the image analysis processing according to the plurality of item information included in the use-notification setting information.

2. The medical image processing device according to claim 1,
- wherein the individual setting information is user information relating to the user.

3. The medical image processing device according to claim 1,
- wherein the individual setting information is patient information of a patient having the subject.

4. The medical image processing device according to claim 1,
- wherein the individual setting information is part information representing a part.

5. The medical image processing device according to claim 1,
- wherein the individual setting information is procedure information representing a procedure performed at a time of acquisition of the medical image.

6. The medical image processing device according to claim 1,
- wherein the processor is further configured to function as a region-of-interest detection unit that detects a region of interest from the medical image as the image analysis processing, and a lesion determination unit that determines lesion information indicating content of a lesion for the region of interest as the image analysis processing, and
- the individual setting information is the lesion information.

7. The medical image processing device according to claim 6,
- wherein the lesion information is a size of the lesion or a type of the lesion.

8. The medical image processing device according to claim 1,
- wherein the notification execution unit performs at least one of an instruction for a screen display output, a sound output instruction, or a vibration output instruction.

9. The medical image processing device according to claim 8,
- wherein the screen display output is an image and/or character information.

10. The medical image processing device according to claim 1,
- wherein the notification execution unit performs a screen display output indicating association between the use-notification setting information and the notification according to an instruction from the user.

11. The medical image processing device according to claim 1,
- wherein the notification setting information includes at least one instruction of an instruction for a screen display output, a sound output instruction, or a vibration output instruction performed by the notification execution unit, and
- the instruction is selected by the user.

12. The medical image processing device according to claim 1,
- wherein the medical image processing device is connected to a medical service support apparatus including an information storage unit in which the patient information and/or diagnosis information is preserved, and
- the notification setting information selection unit selects the use-notification setting information by using the patient information and/or the diagnosis information read from the information storage unit as the individual setting information.

13. The medical image processing device according to claim 12,
- wherein the diagnosis information includes at least one of user information, part information, procedure information, or lesion information.

14. The medical image processing device according to claim 1, further comprising:
- an individual setting information input device that inputs the individual setting information.

* * * * *